United States Patent [19]

Kataoka et al.

[11] Patent Number: 5,442,174
[45] Date of Patent: Aug. 15, 1995

[54] MEASUREMENT OF TRACE ELEMENT CONCENTRATION DISTRIBUTION, AND EVALUATION OF CARRIERS, IN SEMICONDUCTORS, AND PREPARATION OF STANDARD SAMPLES

[75] Inventors: Yuji Kataoka; Yoko Toda, both of Kawasaki, Japan

[73] Assignee: Fujitsu Limited, Kawasaki, Japan

[21] Appl. No.: 137,766

[22] Filed: Oct. 19, 1993

[30] Foreign Application Priority Data

Oct. 23, 1992 [JP] Japan .................................. 4-285783
Aug. 24, 1993 [JP] Japan .................................. 5-209658

[51] Int. Cl.$^6$ .......................................... G01N 23/225
[52] U.S. Cl. ..................................... 250/282; 250/309
[58] Field of Search ......................... 250/282, 288, 309

[56] References Cited

U.S. PATENT DOCUMENTS

5,148,027 9/1992 Umemura et al. ................... 250/309
5,208,457 5/1993 Tsuji ..................................... 250/282

FOREIGN PATENT DOCUMENTS

63-223549 9/1988 Japan .................................... 250/282

OTHER PUBLICATIONS

Klaus Wittmaack, "Surface and Depth Analysis Based on Sputtering", Sputtering by Particle Bombardment III, pp. 196–256 (1991).

*Primary Examiner*—Jack I. Berman
*Attorney, Agent, or Firm*—Armstrong, Westerman Hattori, McLeland & Naughton

[57] ABSTRACT

A concentration distribution in a planar direction or in a depth-wise direction is measured by irradiating an ion containing an alkali metal element as an ion beam onto a solid surface, detecting a three-atom composite ion comprising the irradiated alkali metal ion, an object element, and a base material element from among particles emitted from the solid surface due to sputtering by mass separation, and displaying an intensity distribution of the three-atom composite ion as a two-dimensional image in the case of the concentration distribution in the planar direction or displaying the intensity of the three-atom composite ion with the sputter time in the case of the concentration distribution in the depth-wise direction. A carrier concentration distribution is obtained by irradiating primary ions to the surface of a semiconductor, into which an electrically conductive impurity is introduced, under conditions such that electrically charge up occurs on the surface of the first semiconductor, sequentially measuring the intensity of secondary ions emitted from the surface and having a specific energy level, during the irradiation time, and calculating the concentration distribution from the carrier concentration corresponding to the intensity of the secondary ions and from an etching quantity of the first semiconductor corresponding to the irradiation time of the primary ions.

5 Claims, 24 Drawing Sheets

125 μm X 125 μm

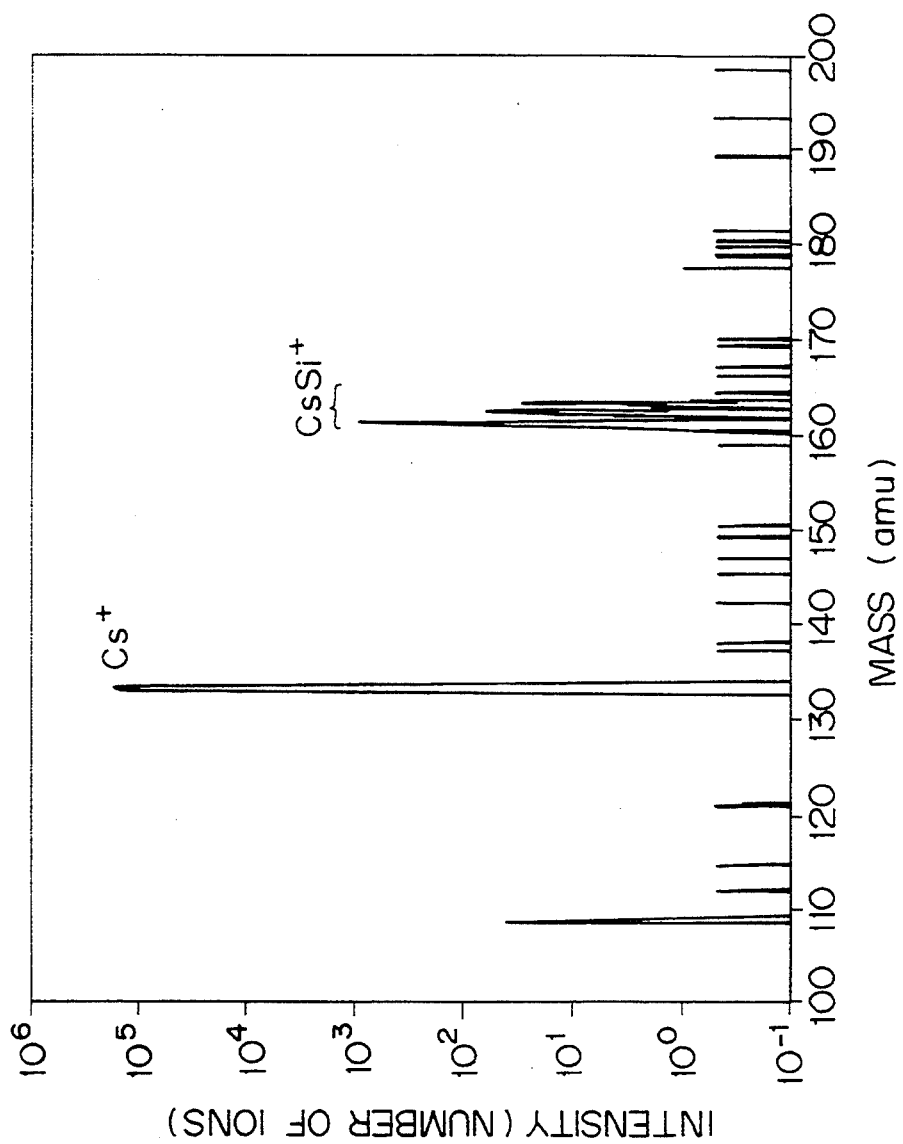

POSITION OF DETECTION OF SECONDARY IONS AT THE TIME OF ANALYSIS IN DEPTH-WISE DIRECTION

● : POLY-Si FILM (DEPTH 63 nm)
○ : POLY-Si FILM (DEPTH 160 nm)
△ : POLY-Si FILM (DEPTH 260 nm)
□ : SILICON SUBSTRATE

POSITION OF DETECTION OF SECONDARY ION AT THE TIME OF ANALYSIS IN DEPTH-WISE DIRECTION

MEASUREMENT OF TRACE ELEMENT CONCENTRATION DISTRIBUTION, AND EVALUATION OF CARRIERS, IN SEMICONDUCTORS, AND PREPARATION OF STANDARD SAMPLES

BACKGROUND OF THE INVENTION

1. Field of the Invention

This invention relates to a method for measuring the concentration distribution of trace elements. More particularly, it relates to a method of analyzing and evaluating, with a high sensitivity and with high resolution, the existence and distribution of trace impurities contained in semiconductor materials, metallic materials, ceramics materials and organic materials in both depth-wise and planar directions.

The present invention also relates to an evaluation method for carriers in semiconductors and a method of preparing a standard sample. Speaking in further detail, the present invention relates to a method of evaluating the carrier concentration and the activation ratio of carriers in semiconductors, for example, by the measurement of the intensity of secondary ions, and a method of preparing standard samples used for this measurement method.

2. Description of the Related Art

Various processes have been attempted, by increasing the impurities in semiconductor materials, metallic materials, ceramic materials, organic materials, and so forth, or by deliberately adding impurity or impurities to them, to improve the material functional properties. However, analysis of trace elements contained in these materials is indispensable for evaluating these processes or evaluating the characteristic properties of the materials.

Secondary ion mass spectrometry (SIMS) analysis has been primarily used in the past as a method of evaluating trace elements existing in these materials, and ordinary methods comprise irradiating $O_2^+$ ions or $Cs^+$ ions to the surface of a sample and detecting monoatomic ions ($M^+$, $M^-$) among the secondary ions emitted by sputtering. According to these methods, however, it has been extremely difficult to correctly and easily determine which elements exist in the film because the matrix effect, under which a detection sensitivity depends on the elementary composition of a base material, and the interface effect, under which the detection sensitivity changes at an interface of layers, are too powerfull. Although a method of detecting a two-atom composite ion ($CsM^+$) between $Cs^+$ and a detection object element (M) has also been proposed, the sensitivity by this method is not high, and this method cannot be applied to the analysis of trace elements. Accordingly, development of a method which can analyze trace elements in a solid has been required.

On the other hand, electronic devices such as Josephson junction devices and MOS ICS use an extremely thin oxide film as a tunnel oxide film or a gate oxide film. In these electronic devices, there exists a large number of problems with device fabrication relating to the oxide film such as the drop in performance such as withstand voltage or breakdown voltage of the oxide film resulting from heat-treatment and breakdown after ion injection, and information on element distribution in the oxide film is extremely important.

Secondary ion mass spectrometry has been employed mainly in the past as an evaluation method of elements existing in the oxide film in the depth-wise direction, and this method generally irradiates $O_2^+$ ions or $Cs^+$ ions to the surface of a sample and detects the monoatomic ions ($M^+$, $M^-$) among the secondary ions emitted by sputtering. According to this method, however, it has been extremely difficult to accurately and easily determine information of the elements existing in the film because the matrix effect, under which the detection sensitivity depends on the elementary composition of the base material, and the interface effect, under which the detection sensitivity changes at the interface between the layers, are very strong. Recently, the method of detecting a two-atom composition ion of $Cs^+$ and an object element has been proposed, but this method does not clarify the angle of incidence of $Cs^+$ onto the sample surface. Accordingly, the reliability of the information thus acquired is not necessarily high.

On the other hand, when an element or elements existing on a fixed surface are to be determined, it has been customary to subject a sample to mass analysis without applying any pre-treatment (formation of an oxide film, etc.) to the sample. For this reason, the detection sensitivity is not sufficiently high, and there are many cases where trace elements, which were originally present, cannot be detected.

In a semiconductor device fabrication process, an electrically conductive impurity such as boron (B) of Group III or phosphorus (P) of Group V is doped into a semiconductor substrate by ion implantation or gas diffusion so as to form a P-type layer or an N-type layer and to obtain transistors, and so forth. To obtain the desired characteristics, control of a carrier concentration distribution is necessary. However, since the concentration distribution and the activation ratio of the conductive impurity change with the introduction method and with the heat-treatment condition, it is very important to correctly detect the carrier concentration distribution.

Spreading resistance analysis (SRA) is generally used at present as an evaluation method of the carrier concentration distribution in the semiconductors. This spreading resistance analysis is the method which brings two or four probes into contact with a sample which is subjected to oblique polish, to measure a resistance value, and converts the resistance value of the sample to the carrier concentration from the relationship of correspondence between the resistance value of a standard sample and a known carrier concentration. To obtain a concentration distribution in the depth-wise direction, further, the probes are sequentially moved on the polished surface in the depth-wise direction, and the resistance value corresponding to the depth is measured.

According to the spreading resistance analysis according to the prior art described above, however, the resistance value to be measured is affected by the crystalline plane orientation. Therefore, when the sample to be measured is polycrystalline, an error of several percent can occur in the measured resistance value. Further, resolution in the depth-wise direction is affected by the accuracy of the oblique polishing. Accordingly, the depth resolution is about 10 nm and an improvement in this resolution has been desired.

Further, secondary ion mass spectrometry (SIMS) is known as a method of measuring the quantity of conductive impurities. Generally, this method comprises bombarding oxygen ions, for example, as the primary ions to the sample to be measured, measuring the intensity of the secondary ions emitted from the sample, and specifying the quantity of the conductive impurity of the sample from the relationship between the intensity of the secondary ions of the standard sample having a known quantity of the conductive impurity and the quantity of the known conductive impurity. However, according to this method, an error occurs in the converted quantity of the conductive impurity if the standard sample is electrically charged and, eventually, an error occurs in the measured quantity of the conductive impurity. Though this method can measure the concentration distribution of the conductive impurity, it cannot measure the carrier concentration distribution.

SUMMARY OF THE INVENTION

The present invention is directed to make a contribution to the evaluation of functional properties of materials by effecting a high-sensitivity analysis and a high-resolution analysis of trace impurities contained in semiconductor materials, metallic materials, ceramic materials and organic materials in both depth-wise and planar directions.

The present invention is further directed to make a contribution to the evaluation of characteristics of electronic devices by accurately evaluating a concentration distribution of elements existing in an oxide film, in a depth-wise direction, existing on the surface of, and between layers of, materials used for the electronic devices.

The present invention is further directed to determine with a high sensitivity the trace elements existing on the fixed surface.

The present invention is further directed to provide an evaluation method of carriers in semiconductors capable of improving the accuracy of carrier concentration distribution and depth resolution measurements, and a method of preparing a standard sample.

To accomplish the objects described above, the first invention (claim 1) of the present application provides a method of measuring the concentration distribution of trace elements in a solid in a planar direction and/or in a depth-wise direction, which comprises irradiating ions containing alkali metal elements such as Li, Cs, etc., as an ion beam onto a solid surface, detecting a three-atom composite ion consisting of an irradiated alkali metal ion, an object element, and a base material element, from among the particles emitted from the solid surface by sputtering, by mass separation, and measuring a concentration distribution, in the planar direction, by displaying an intensity distribution of the three-atom composite ion as a two-dimensional image, or measuring the concentration, in the depth-wise direction, by displaying the intensity of the three-atom composite ion with the sputtering time.

The first embodiment of the second invention of the present application relates to a method of measuring a concentration distribution of trace elements existing in a solid in a planar direction and/or a depth-wise direction, which comprises irradiating an oxygen beam to a solid surface and simultaneously irradiating an ion beam containing an alkali metal element such as Li, Cs, etc., as an ion beam at an angle of incidence of from 30° to 60° with respect to a normal direction of the sample so as to carry out sputtering, while forming an oxide on the solid surface, detecting a two-atom composite ion comprising the alkali metal ion and the object element by mass separation from the particles emitted from the solid surface, and then measuring the concentration distribution in a planar direction by displaying the intensity of the two-atom composite ion as a two-dimensional image, or measuring the concentration distribution in the depth-wise direction by displaying the intensity of the two-atom composite ion with the sputtering time.

The second embodiment of the second invention of the present application relates to a method of measuring a concentration distribution of trace elements existing in a solid in a planar direction and/or a depth-wise direction, which comprises alternately repeating irradiation of an oxygen ion beam and irradiation of an ion beam containing an alkali metal element such as Li, Cs, etc., (at an angle of incidence of from 30° to 60° with respect to the normal of the sample), carrying out sputtering while forming an oxide surface on the solid surface, detecting a two-atom composite ion comprising the alkali metal ion and an object ion by mass separation from among the particles emitted from the solid surface, and then measuring the concentration distribution in the planar direction by displaying the intensity of the two-atom composite ion as a two-dimensional image, or measuring the concentration distribution in the depth-wise direction by displaying the intensity of the two atom composite ion with respect to the sputter time.

Further, the third invention (Example 4) according to the present application relates to a method of measuring a concentration distribution of a trace element existing in an oxide film in a depth-wise direction, which comprises irradiating an alkali metal ion such as $Cs^+$, $Li^+$, etc., onto a solid surface or a solid sample in which an oxide film exists between the layers thereof, at an angle of incidence of from 60° to 90° with respect to the direction of the normal of a sample, detecting a two-atom composite ion comprising the irradiated alkali ion and an object element (M) by mass separation from the secondary ions emitted by sputtering, and measuring the concentration distribution in the depth-wise direction by displaying the intensity of the two-atom composite ion with respect to the sputter time.

Further, the fourth invention (Example 5) of the present application relates to a method of detecting an element existing on a solid surface, which comprises forming an extremely thin oxide film on the solid surface, irradiating an ion beam containing an alkali metal element such as Li, Cs, etc., at an angle of incidence of 30° to 60° with respect to the normal of the sample, detecting a two-atom composite ion comprising the irradiated alkali metal ion and the element existing on the solid surface and mass-analyzing the same.

The fifth invention (Examples 6, 8) according to the present application provides an evaluation method of a carrier inside a semiconductor which comprises irradiating a primary ion to the surface of a first semiconductor into which an electrically conductive impurity is introduced, under a condition such that electrical charge up takes place on the surface, sequentially measuring the intensity of a secondary ion emitted from the surface and having specific energy, with the passage of the irradiation time of the primary ion and obtaining a carrier concentration distribution in the semiconductor in the depth-wise direction from the carrier concentration corresponding to the intensity of the secondary ion and from an etching quantity of the first semiconductor corresponding to the irradiation time of the primary ion.

The sixth invention (Example 7) according to the present application provides a method of evaluating a carrier inside a semiconductor which comprises irradiating a primary ion onto the surface of a second semiconductor into which an electrically conductive impurity is introduced under the same condition where an electrically conductive impurity is introduced into a first semiconductor, under a condition such that electrically charge up does not take place on the surface, measuring the intensity of the secondary ion emitted from the surface so as to acquire the concentration distribution of the conductive impurity in the second semiconductor in the depth-wise direction, and acquiring an activation ratio using the concentration distribution of the conductive impurity in the second semiconductor and the carrier concentration distribution in the first semiconductor.

The seventh invention (Examples 6, 7) according to the present application provides a method of preparating a standard sample used for converting the intensity of secondary ions emitted from a semiconductor by the irradiation of a primary ion to the semiconductor having an electrically conductive impurity implanted thereto, to a carrier concentration or a conductive impurity concentration, which comprises introducing in advance an electrically conductive impurity into a semiconductor to serve as a standard sample so as to lower the resistivity of the conductor, and introducing an electrically conductive impurity having a known quantity into the semiconductor described above.

BRIEF DESCRIPTION OF THE DRAWINGS

FIG. 14 is a graph showing an analysis result according to the prior art;

DESCRIPTION OF THE PREFERRED EMBODIMENTS

Figure 1:
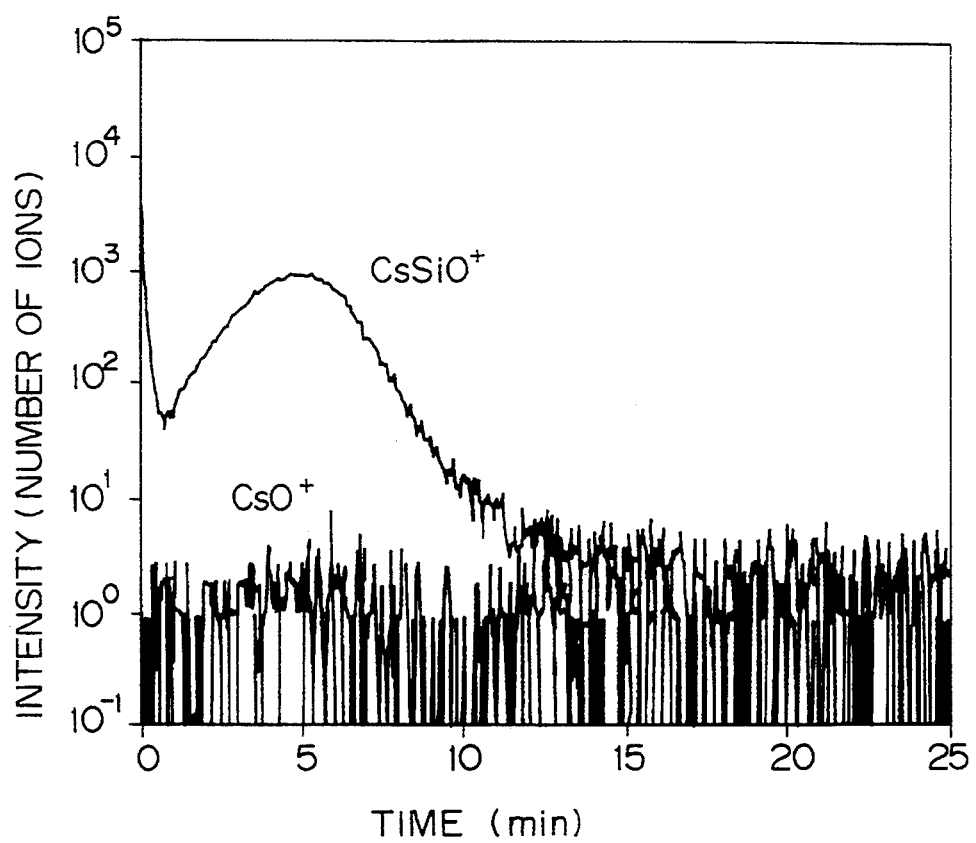
FIG. 1 is a graph showing a concentration distribution of O in Si in a depth-wise direction.

In the first invention of the present invention, a method which sets an angle of incidence of an irradiation ion beam to 30° to 90° with respect to the direction of the normal of a sample so as to improve the sensitivity (claim 2) is preferred. Further, a method which sets the angle of incidence of the irradiation ion beam to 60° to 90° with respect to the direction of the normal of the sample is preferred so as to improve the resolution in a depth-wise direction (claim 3).

To improve resolution in a planar direction, a method which sets the angle of incidence of the irradiation ion beam to 0° to 30° to the direction of the normal of the sample (claim 4) is preferred.

In other words, the ion beam is scanned so as to catch an image of the secondary ion, but when the angle of incidence is tilted, the beam shape becomes elliptic on the sample surface. To obtain an image having high resolution, the beam shape on the sample surface must be made sharp, and a suitable inclination is within 30°.

To analyze trace elements contained in an oxide film with a high sensitivity, the angle of incidence of an irradiation alkali metal ion beam is preferably set to 60° to 90° to a solid surface having the oxide film on the surface or between layers thereof (claim 5).

As described above, according to the first invention, the angle of incidence of the ion beam incident into the solid is suitably selected in accordance with the respective objects such as high sensitivity analysis, mass spectrometry with high resolution, analysis with high planar resolution, analysis of the oxide film, and so forth.

According to the means described above, the problems of the matrix effect and the interface effect that have been the problems with the prior art methods can be eliminated, and high-sensitivity, high-resolution analysis becomes possible in accordance with the intended object.

According to the first embodiment of the second invention, the oxygen ion and the alkali metal ion are simultaneously irradiated under the condition such that the injection depth of the oxygen ion is greater than that of the alkali metal ion. This condition can be determined by considering the acceleration energy and the angle of incidence of the oxygen ion.

Alternatively, this condition can be obtained through the acceleration energy of the alkali metal ion (or even by limiting the angle of incidence of the alkali metal ion to 30° to 60°).

According to "Secondary Ion Mass Spectrometry" by Robert G. Wilson, Fred A. Stevie and Charles W. Magee (John Wiley & Sons Publication, 1989), p 1.2-1, the injection depths of $O_2^+$, $Ar^+$ and $Cs^+$ are given by the following formulas I to III, respectively:

$$O_2^+: R = 2.15 E \cos \theta \qquad (I)$$

$$Ar^+: R = 1.622 E^{0.84} \cos \theta \qquad (II)$$

$$Cs^+: R = 1.838 E^{0.64} \cos \theta \qquad (III)$$

(where R is a penetration depth (nm), $\theta$ is an angle of incidence from normal, and E is primary energy (keV)). Accordingly, condition setting is easy.

In the second embodiment, the thickness of the oxide film formed on the sample surface is preferably from 2 to 5 nm.

As described above, the second invention of the present application provides a method which forms an extremely thin oxide film having a thickness of 2 to 5 nm on the solid surface by vacuum deposition, etc., and irradiates an ion beam containing alkali metal such as Li, Cs, etc., in the presence of this ultra-thin oxide film at the angle of incidence of 30 to 60 degrees. During detection, this method catches two-atom composite ions comprising the alkali metal ion and the object element from among the particles emitted from the solid surface due to sputtering, and effects mass analysis of the composite ions so as to evaluate the concentration distribution of the detection object element in both the depth-wise direction and the planar direction.

According to the means described above, the matrix effect and the interface effect that have been the problems with the prior art methods can be eliminated and high-sensitivity analysis becomes possible.

The third method of the present invention conducts mass analysis for the solid sample existing on the surface or between the layers by the method described above, and can accurately measure the concentration distribution of the elements existing in the film in the depth-wise direction. Therefore, the third method can make contribution to the evaluation of the characteristics of electronic devices.

The fourth invention (Example 5) forms in advance an oxide film on a sample surface and then irradiates ions containing an alkali metal element at a predetermined angle. In this way, the fourth invention can enhance the sensitivity and determines the trace elements existing on the solid surface.

An evaluation method of a carrier of a semiconductor according to the present invention (Examples 6, 8) irradiates primary ions on the surface of the semiconductor under conditions such that electrical charge up occurs on the surface of the semiconductor, sequentially measures the intensity of the secondary ions jumping out from the semiconductor and having specific energy with the passage of the irradiation time of the primary ions, and acquires the carrier concentration distribution in the semiconductor in the depth-wise direction from a carrier concentration corresponding to the intensity of the secondary ions and an etching quantity of the semiconductor corresponding to the irradiation time of the primary ions.

The present invention utilizes the property that the charge quantity at the surface of the semiconductor depends on the resistivity of the semiconductor surface, that is, on the carrier concentration of the semiconductor surface. In other words, the present invention irradiates the primary ions under the condition such that the semiconductor surface is electrically charged up, and controls the intensity of the secondary ions having specific energy. Now, the energy distribution of the secondary ions irradiated depends on the charge quantity and shifts to the high energy side or to the low energy side. For this reason, a certain specific correlationship develops between the carrier concentration of the semiconductor surface and the shift quantity of the energy distribution of the secondary ion intensity. Since the shape of the energy distribution of the secondary ion intensity is hardly affected by the shift in the energy distribution, the intensity of the secondary ions corresponding to the carrier concentration can be measured by measuring the intensity of the secondary ions having specific energy.

Accordingly, the carrier concentration distribution in the semiconductor in the depth-wise direction can be obtained by converting the intensity of the secondary ions measured with the passage of the irradiation time of the primary ions to the carrier concentration.

Since the etching quantity due to the irradiation of the primary ions is used to detect the position in the depth-wise direction, higher accuracy can be obtained than the spreading resistance analysis method using the polishing method according to the prior art.

A standard sample having a known quantity of a known impurity concentration is used for the conversion from the secondary ion intensity to the carrier concentration. In this case, if the energy distribution of the secondary ion intensity shifts because the standard sample is electrically charged up, an error occurs in the converted carrier concentration. Accordingly, it is necessary to prevent the standard sample from being electrically charged up.

In the preparation method of the standard sample according to the present invention, another conductive impurity is in advance introduced before the introduction of the known quantity of the conductive impurity into the semiconductor as the standard sample so as to lower the resistivity of the semiconductor as the standard sample.

Accordingly, even when the concentration of the known quantity of the conductive impurity to be introduced into the semiconductor is low, electrically charge up does not occur at the time of the irradiation of the primary ion, and the intensity of the secondary ions can be measured with a high level of accuracy. For this reason, the known quantity of the conductive impurity in the standard sample is accurately acquired.

Having the construction described above, the present invention can analyze with a high sensitivity the trace elements contained in semiconductor materials, metallic materials, ceramic materials and in organic materials in both the depth-wise direction and the planar direction, and can make a contribution to the evaluation of functional properties of these materials. Further, the present invention can accurately measure the elements existing in the oxide film used in the electronic devices in the depth-wise direction and can thus make a contribution to the evaluation of the characteristics of electronic devices.

The evaluation method of the carrier of the semiconductor according to the present invention utilizes the facts that when irradiated with the primary ions at a specific angle of incidence, the polysilicon film 3 (FIG. 15) is charged electrically and that the carrier concentration and the charge quantity of the polysilicon film 3 have the relation of mutual dependence, and provides correlationship between the carrier concentration and the shift quantity of the energy distribution of the secondary ion intensity.

Accordingly, the carrier concentration distribution in the polysilicon film in the depth-wise direction can be obtained by measuring the intensity of the secondary ions having specific energy with the passage of the irradiation time of the primary ions and further converting it to the carrier concentration.

Since the present invention uses the etching quantity due to the irradiation of the primary ions for determining the position in the depth-wise direction, the present invention provides higher accuracy than the spreading resistance analysis method using the polishing method.

Furthermore, in the preparation method of the standard sample according to the present invention, another conductive impurity is in advance introduced before the introduction of the known quantity of the conductive impurity so as to lower the resistivity of the substrate of the standard sample.

Accordingly, even when the concentration of the known quantity of the conductive impurity to be introduced into the standard sample is low, electrical charge up does not occur at the time of the irradiation of the primary ions, so that the intensity of the secondary ions can be measured precisely and, eventually, the concentration of the known quantity of the conductive impurity can be obtained precisely.

Hereinafter, the present invention will be explained in further detail with reference to Examples thereof, but the invention is not naturally limited thereto.

EXAMPLE 1

Relating to the First Invention (Claim 1)

Figure 2:
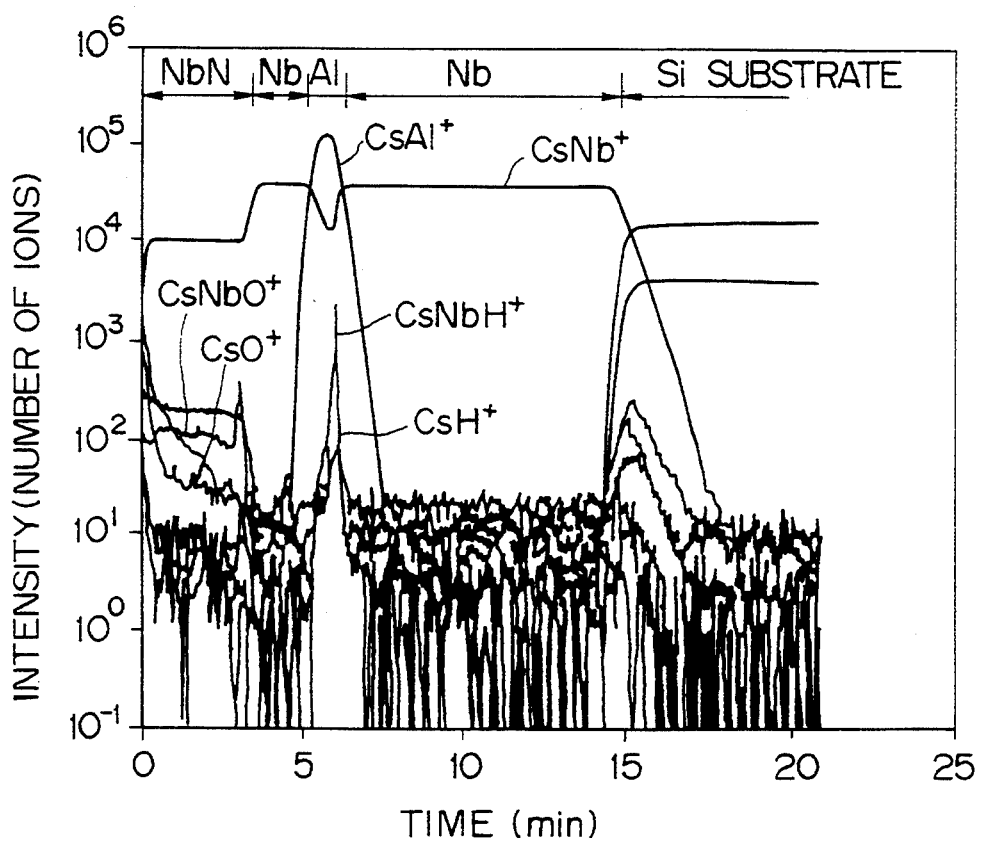
FIG. 2 is a graph showing a distribution of O and H in an NbN/Nb/Al/Nb/Si substrate in a depth-wise direction.

A sample was produced by ion-implanting $^{18}O^+$ into an Si substrate at 100 keV in a dose of $5 \times 10^{14}$ atoms/cm$^2$. Next, Cs$^+$ ion beam was irradiated to this sample surface at an angle of incidence of 54° so as to increase its sensitivity. The result is shown in FIG. 1. It can be understood from FIG. 1 that detection of CsSiO$^+$ (Mass 177.0 amu) had a much higher sensitivity than the detection of CsO$^+$ (Mass 148.9 amu) according to the prior art method. FIG. 2 shows the result of measurement of the concentration distributions of O and H in the depth-wise direction in the structure of an NbN/Nb/Al/Nb/Si substrate, and Cs$^+$ ion beam was irradiated at an angle of incidence of 72° in order to obtain high resolution in the depth-wise direction. Since the detection of CsNbO$^+$ (Mass 241.8 amu), CsNbH$^+$ (Mass 226.8 amu) had a higher sensitivity than the detection of CsO$^+$, CsH$^+$ (Mass 133.9 amu) according to the prior art and the distribution on the interface between the layers could be acquired more distinctively, resolution in the depth-wise direction, too, was higher.

Next, the detection limit of $^{18}O^+$ in Si determined from the sample obtained by $^{18}O^+$ ion implantation into the Si substrate is shown in Table 1.

TABLE 1

| angle of incidence (°) | Detection limit of O in Si detection limit (cm$^{-3}$) |
|---|---|
| 36 | $7.0 \times 10^{17}$ |
| 45 | $7.0 \times 10^{16}$ |
| 54 | $5.0 \times 10^{16}$ |
| 60 | $6.0 \times 10^{16}$ |
| 72 | $2.5 \times 10^{17}$ |
| 80 | $5.0 \times 10^{17}$ |

As is obvious from the result tabulated in Table 1, it was preferred to set the incident angle of the irradiation ion beam to 30° to 90°, particularly 45° to 60°, with respect to the normal of the sample, in order to improve the sensitivity.

EXAMPLE 2

The First Invention (Claim 1)

Figure 3:
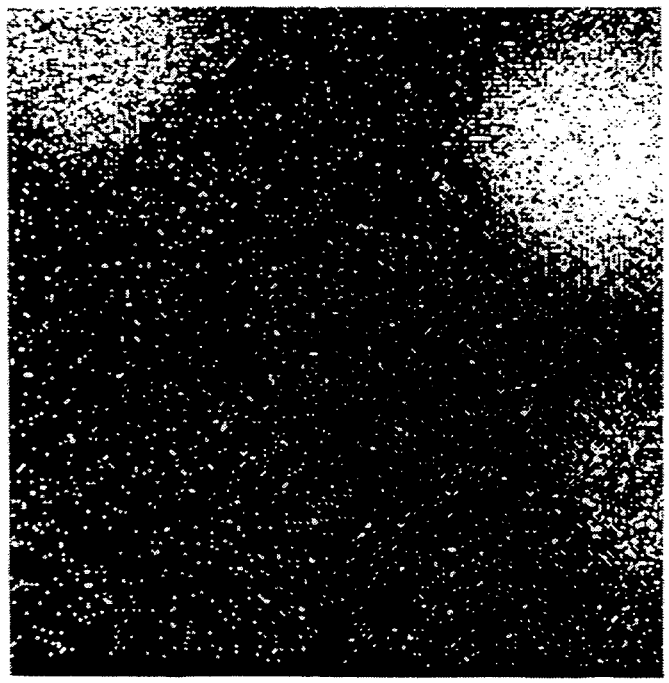
FIG. 3 shows a secondary ion image on an Si substrate surface.

CsSiO$^+$ was detected in foreign matter on the surface of the Si substrate by the use of Cs$^+$ ion beam as the primary ions. A Cs$^+$ ion beam having a diameter of about 10 μm was scanned on the substrate surface in an X-Y direction, and the intensity of CsSiO$^+$ was displayed as a secondary ion image with the x-y position. FIG. 3 shows the resulting secondary ion image. White portions indicate that the intensity of CsSiO$^+$ was high and that O existed in the foreign matter.

EXAMPLE 3

Relating to the Second Invention

Next, an example of the invention wherein the irradiation of the oxygen ion beam and the alkali metal element ion beam was alternately repeated will be illustrated.

Figure 4:
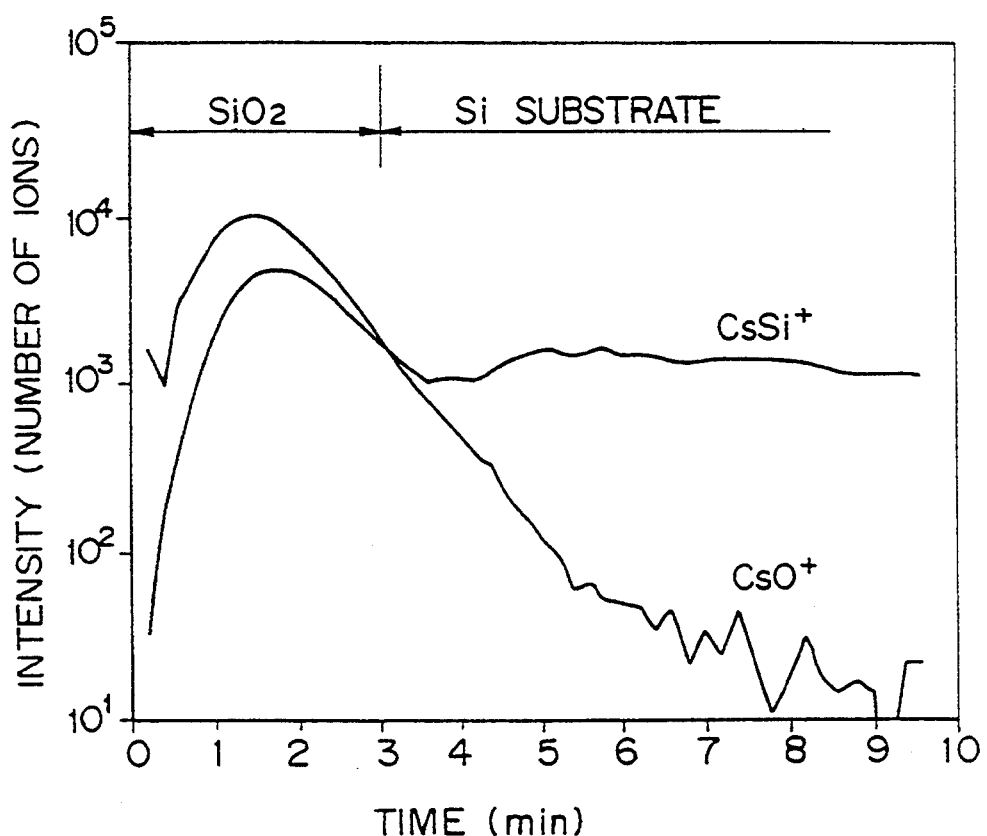
FIG. 4 is a graph showing a concentration distribution of O and Si in a depth-wise direction by irradiation with $Cs^+$.
Figure 5:
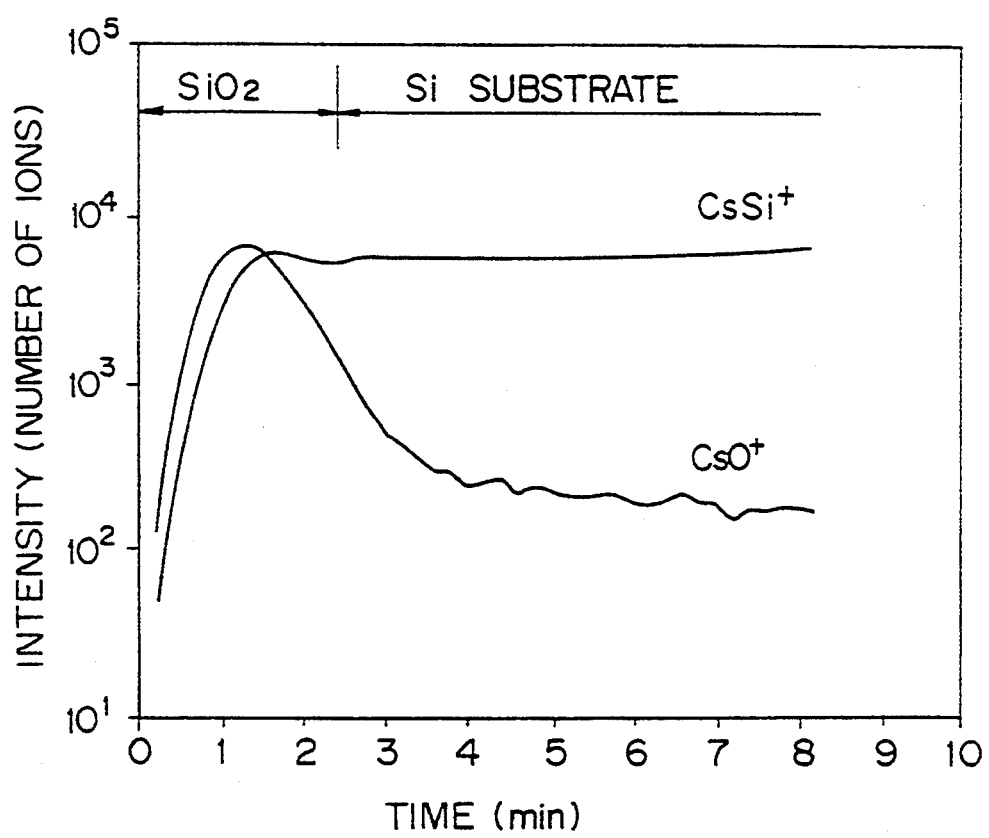
FIG. 5 is a graph showing a concentration distribution of O and Si in a depth-wise direction by alternate irradiation with $O_2^+$ and $Cs^+$.

FIGS. 4 and 5 show the results of measurement of the concentration distribution of O and Si in the depth-wise direction using a sample obtained by forming a 5 nm-thick SiO$_2$ on an Si (100) substrate by thermal oxidation. FIG. 4 shows a concentration distribution obtained by using only an ion beam containing an alkali metal (Cs$^+$ beam) (according to the prior art), and FIG. 5 shows the concentration distribution obtained by the alternate irradiation of the oxygen ion beam and the ion beam containing the alkali metal (Cs$^+$ beam). The angle of incidence of the Cs$^+$ beam was 30° in FIG. 4 and that of Ce$^+$ ion beam and O$^+$ ion beam was 60° respectively in FIG. 5, and a two-atom composite ion comprising Cs and the object element was detected. Whereas the intensity of CsSi$^+$ in the Si substrate was $1 \times 10^3$ count in FIG. 4, it was $5 \times 10^3$ count in FIG. 5, and the sensitivity could be improved five times. Accordingly, when any trace elements existed in the Si substrate, the present invention could detect them with a sensitivity which was by five times higher than the prior art method.

In this second invention, the thickness of the oxide film to be formed on the sample surface at the time of analysis was preferably from 2 to 5 nm.

Figure 6:
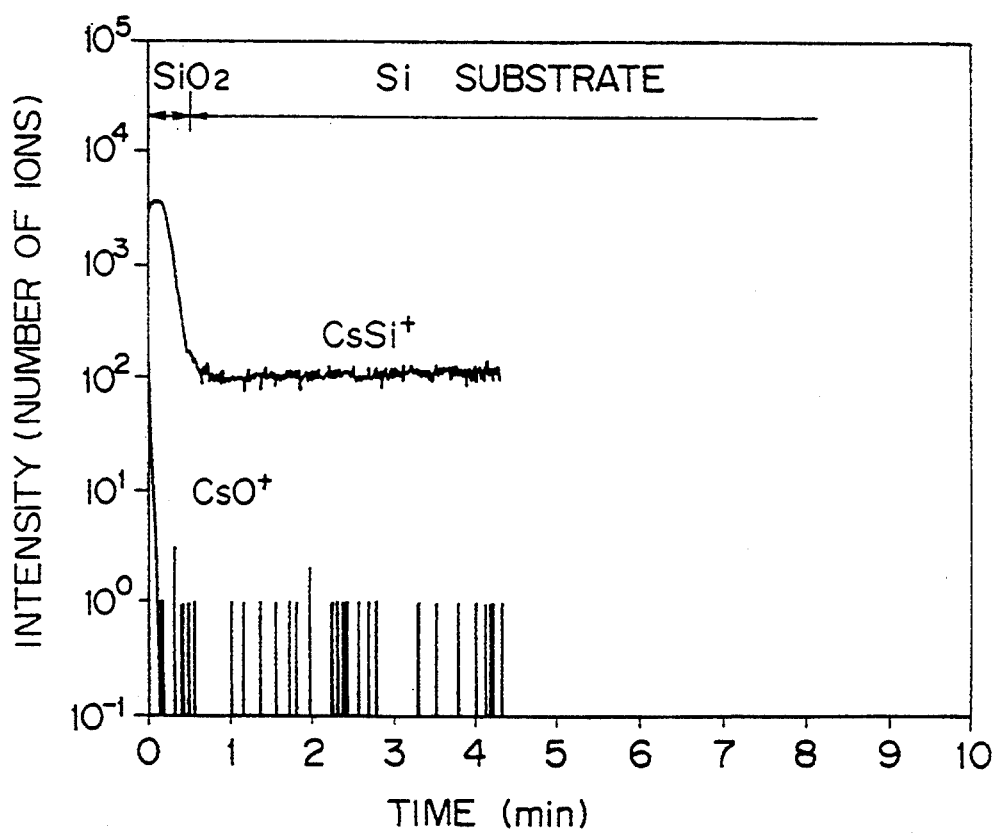
FIG. 6 is a graph showing a concentration distribution of O and Si in a depth-wise direction by irradiation with $Cs^+$.
Figure 7:
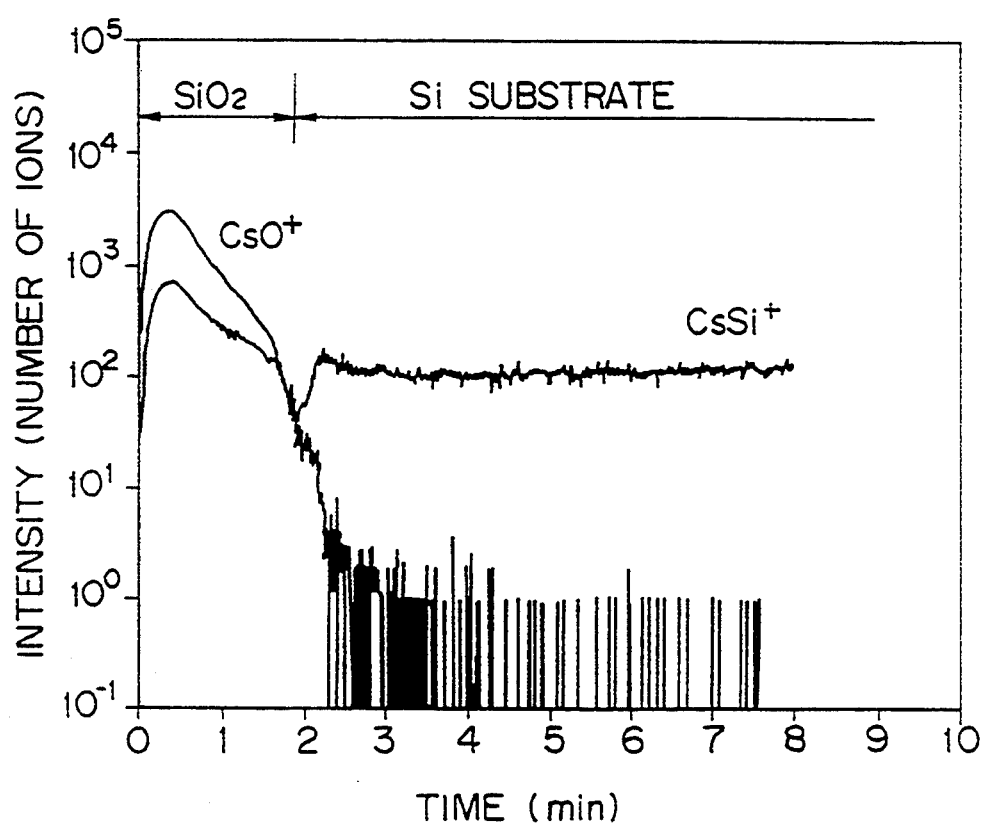
FIG. 7 is a graph showing a concentration distribution of O and Si in a depth-wise direction by irradiation with $Cs^+$.

FIG. 7 shows a concentration distribution of Si in the depth-wise direction of a sample produced in Example 3 wherein the thickness of SiO$_2$ was 10 nm. FIG. 6 shows the concentration distribution of O and Si in the depth-wise direction in the sample of FIG. 7 wherein the thickness of SiO$_2$ was changed to 2 nm by HF etching. The change of the intensity of CsSi+ shown in FIG. 4 could also be observed in FIGS. 6 and 7, too. However, in FIG. 7, the intensity of CsSi+ gradually dropped towards the SiO2/Si substrate interface in FIG. 7. The thickness at which the effect of the oxide film could be observed was up to about 5 nm which was a half of 10 nm. When the thickness of the oxide film was smaller than 2 nm, the concentration of the alkali metal ion to be irradiated in common in either case did not reach a predetermined level (the state where sputtering was not steady), the effect of the present method was believed low. Accordingly, the thickness of the oxide film to be formed on the sample surface during analysis according to the present invention was preferably limited to from 2 to 5 nm.

EXAMPLE 4

Relating to the Third Invention

Figure 8:
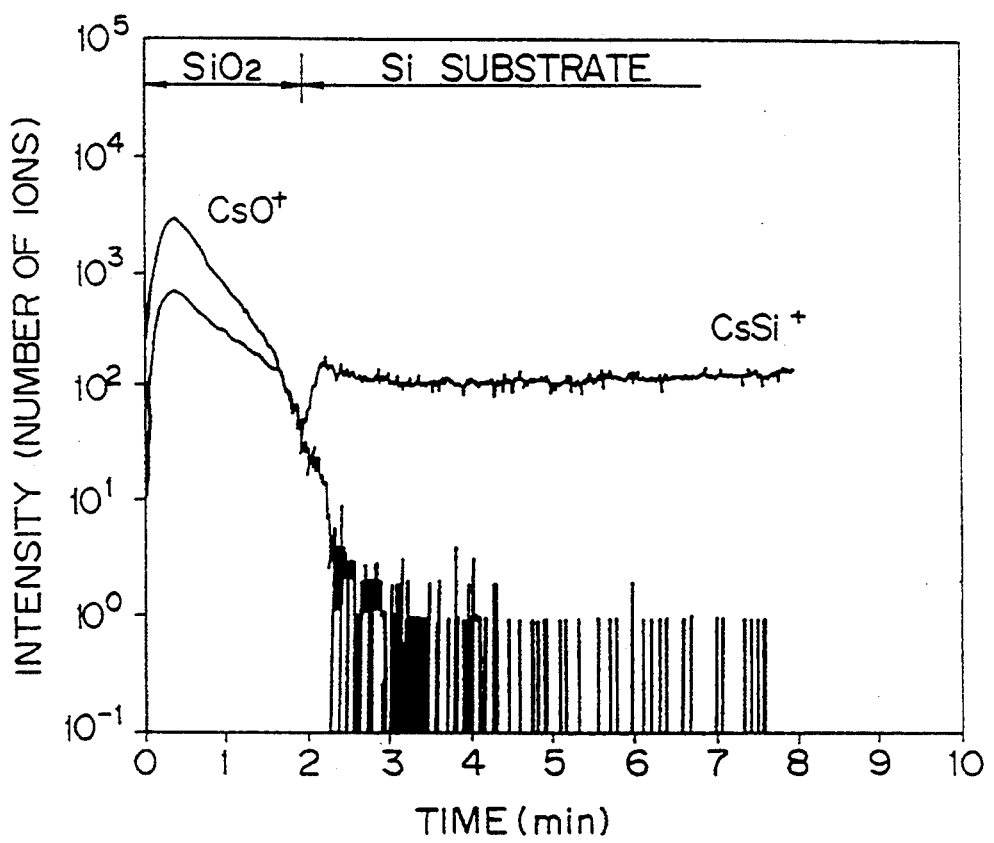
FIG. 8 is a graph showing a concentration distribution of O and Si in a depth-wise direction (at an angle of incidence of $Cs^+$ of 30°)
Figure 9:
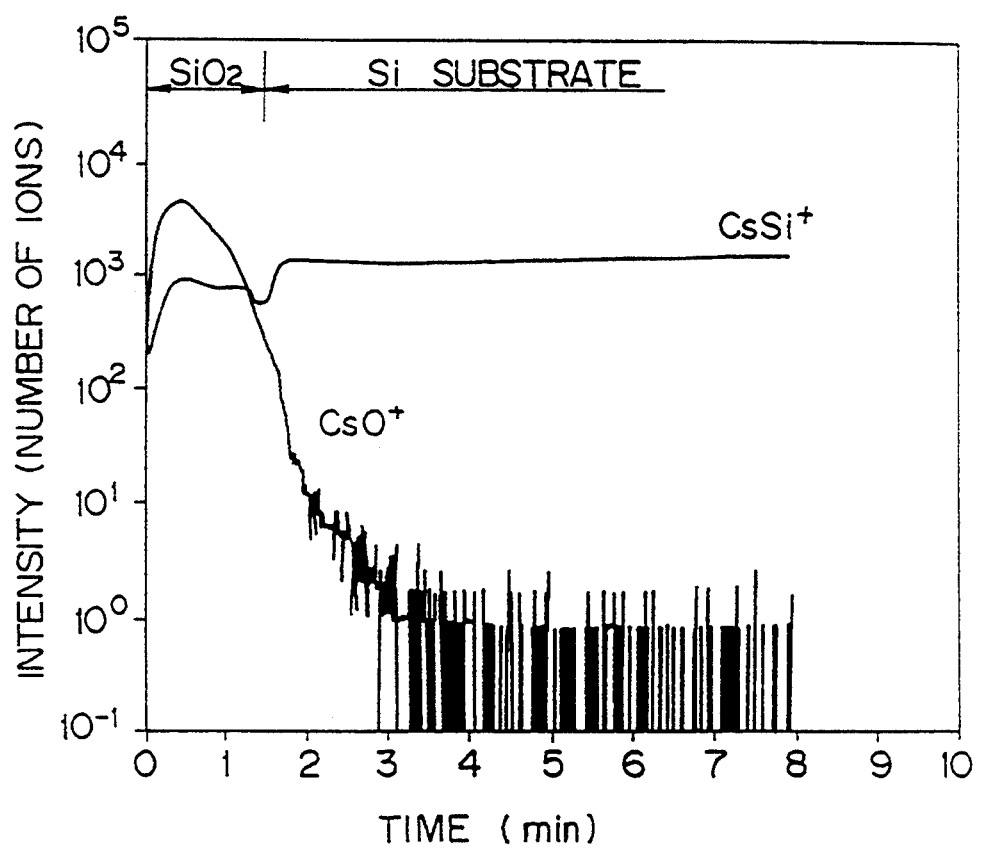
FIG. 9 is a graph showing a concentration distribution of O and Si in a depth-wise direction (at an angle of incidence of $Cs^+$ of 45°)
Figure 10:
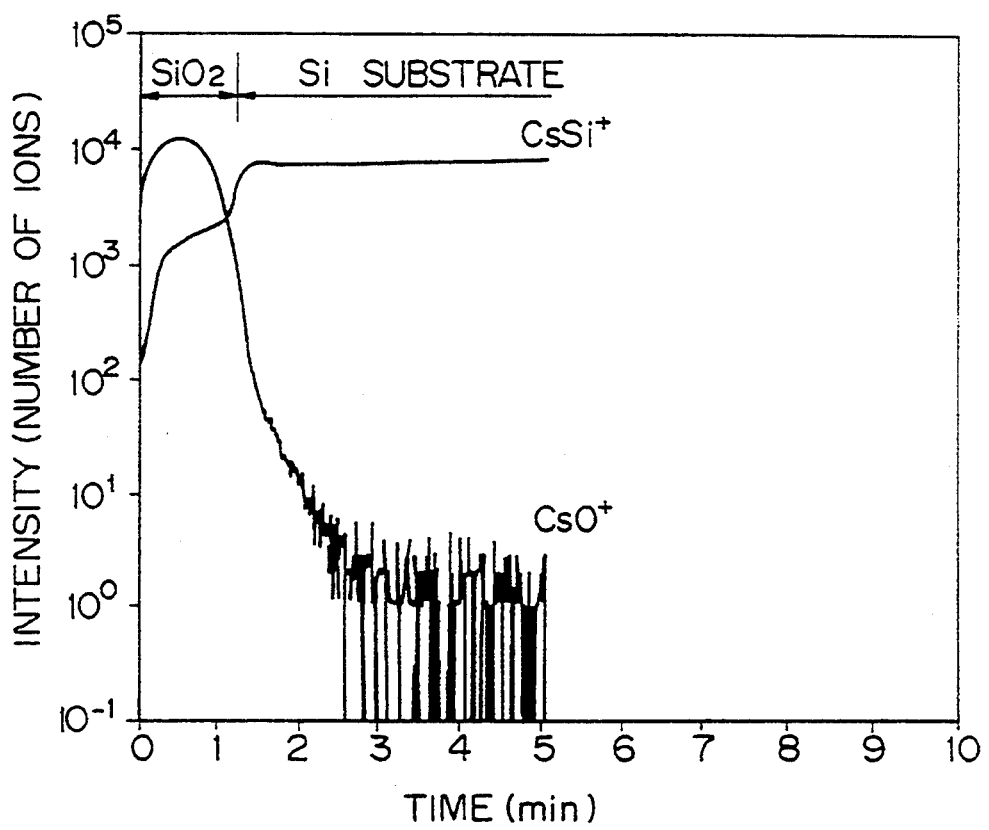
FIG. 10 is a graph showing a concentration distribution of O and Si in a depth-wise direction (at an angle of incidence of $Cs^+$ of 60°)
Figure 11:
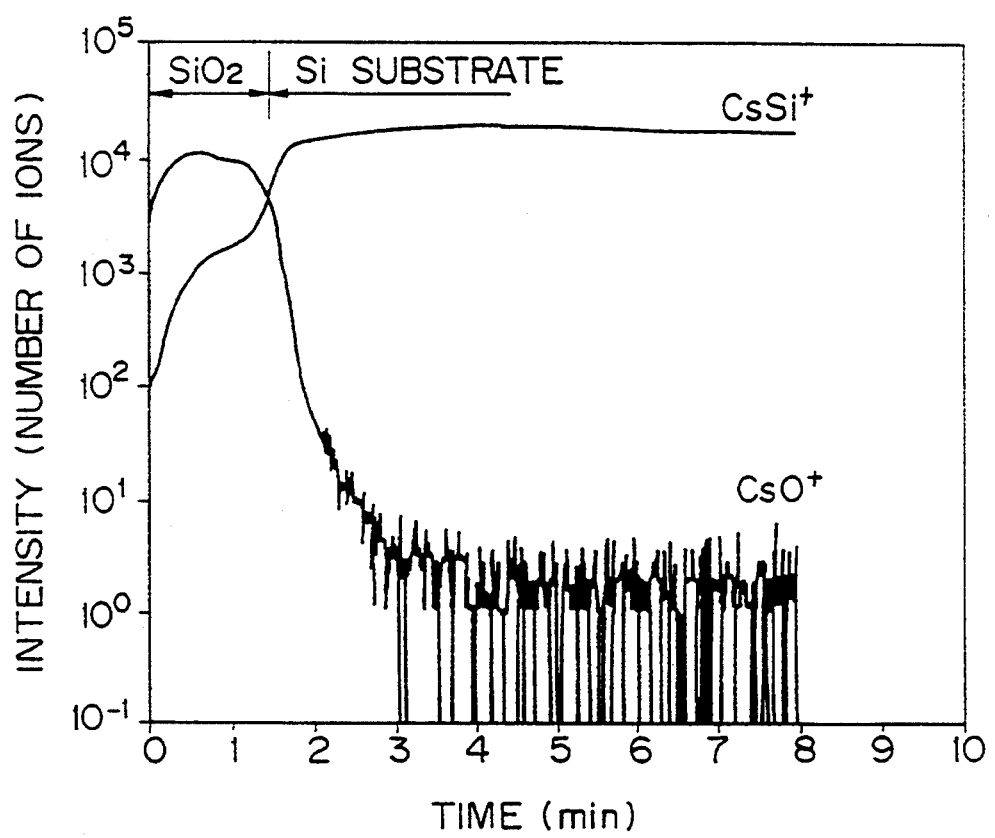
FIG. 11 is a graph showing a concentration distribution of O and Si in a depth-wise direction (at an angle of incidence of $Cs^+$ of 80°)

FIGS. 8 to 11 show the results when the alkali metal ion Cs+ was irradiated to a sample obtained by forming $SiO_2$ to a thickness of 10 nm on the Si substrate, by changing the angle of incidence of Cs+ ion beam to the sample surface to 30°, 45°, 60° and 80°, and two-atom composite ion CsSi+ and CsO+ was detected. In FIGS. 8 and 9, the secondary ion intensity of CsSi+ and CsO+ in $SiO_2$ decreased from the sample surface towards the $SiO_2/Si$ substrate interface and the profile of CsSi+ in the depth-wise direction was discontinuous on the $SiO_2/Si$ substrate interface. On the other hand, in FIGS. 9 to 11, particularly in FIGS. 10 and 11, the intensity of the secondary ions of CsSi+ and CsO+ in $SiO_2$ was substantially constant and no discontinuous portions existed in both of them in the depth-wise direction. It could be understood from these results that the concentration distribution of the element existing in the oxide film in the depth-wise direction could be measured accurately by irradiating Cs+ at an angle of incidence ranging from 60° to 90° to the sample surface and detecting CsM+ as shown in FIGS. 10 and 11.

EXAMPLE 5

Relating to the Fourth Invention

Figure 12:
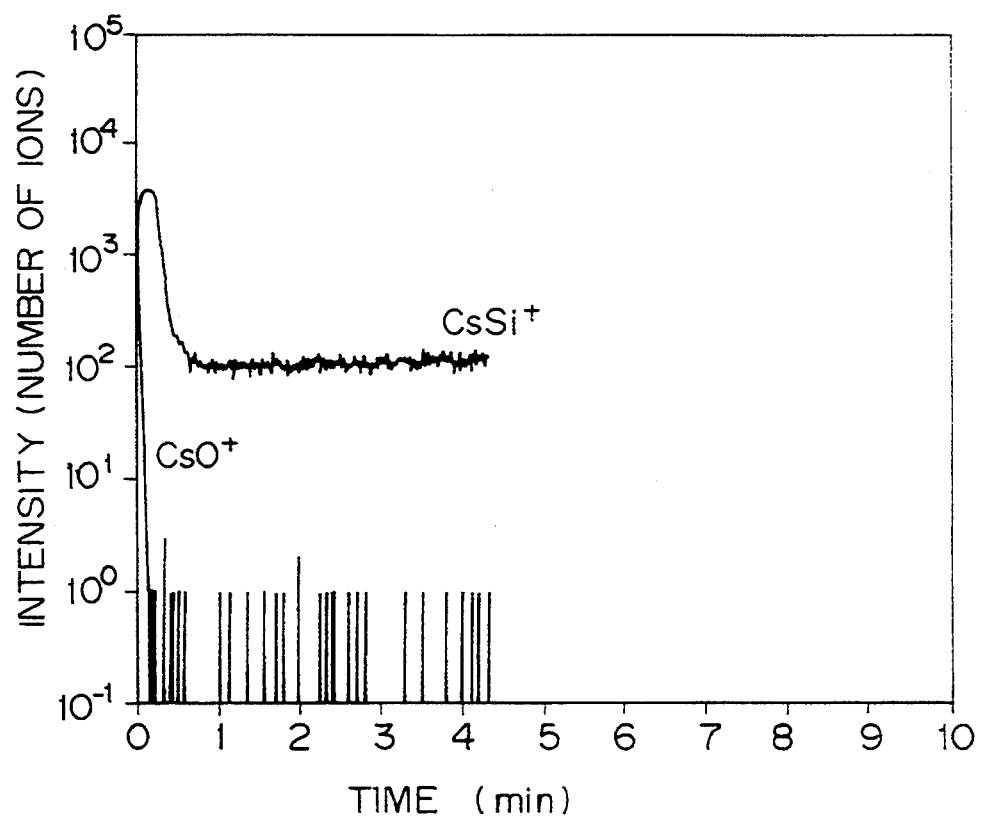
FIG. 12 is a graph showing a measurement result after $SiO_2$ is formed on the Si surface.

I) After a 2 nm-thick $SiO_2$ film was formed on the Si substrate surface, Cs+ was irradiated at an angle of incidence of 30°. FIG. 12 shows the result of detection of the ions (CsSi+ and CsO+) emitted from the solid surface due to the sputtering. It can be understood from FIG. 12 that the CsSi+ intensity on the sample surface increased due to the influence of the oxide film.

Figure 13:
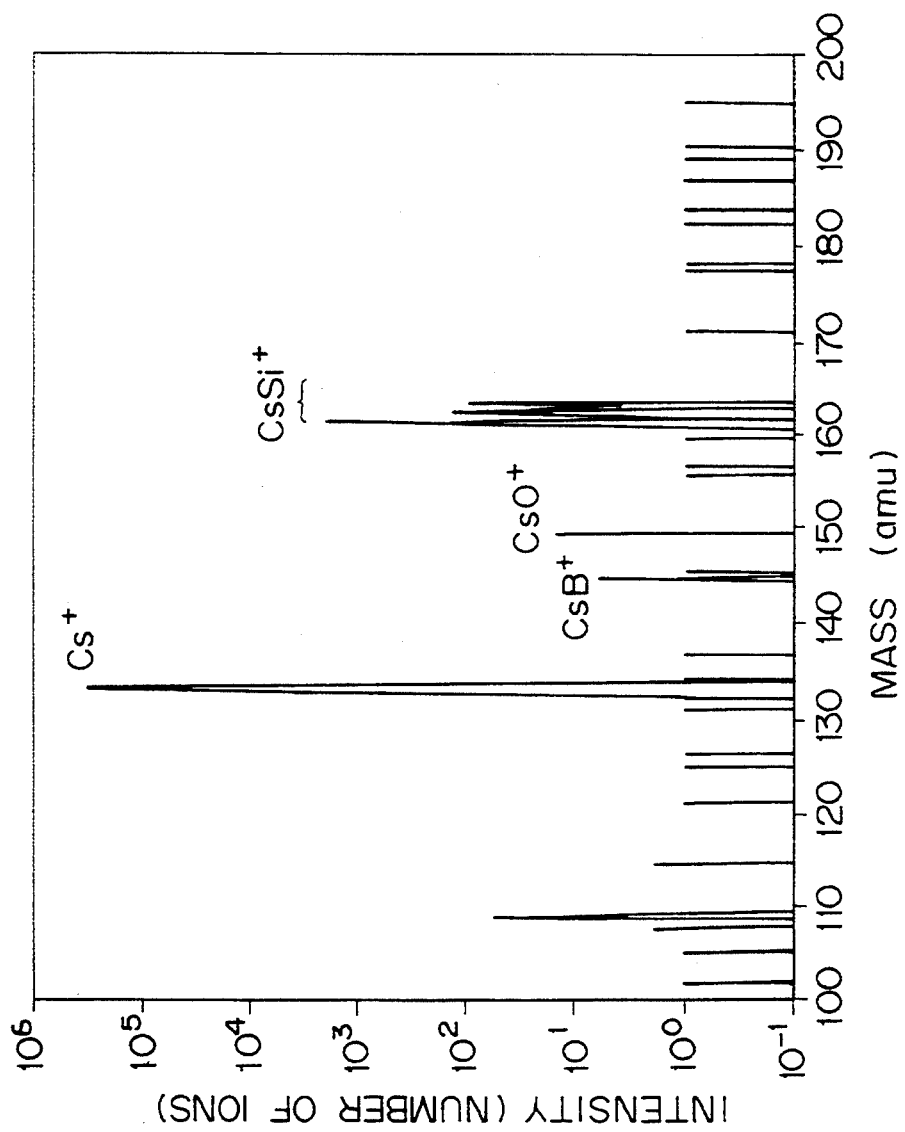
FIG. 13 is a graph showing an analysis result according to the fourth embodiment.

II) FIGS. 13 and 14 show mass spectrograms of the sample obtained by doping B into the Si substrate. FIG. 14 shows the result according to the prior art method and FIG. 13 shows the result according to the present method (the method which first formed the thin oxide film on the sample surface and then made an analysis). Whereas B (boron) was detected as CsB+ in FIG. 13, B could not be detected in FIG. 14.

EXAMPLE 6

Figure 20A:
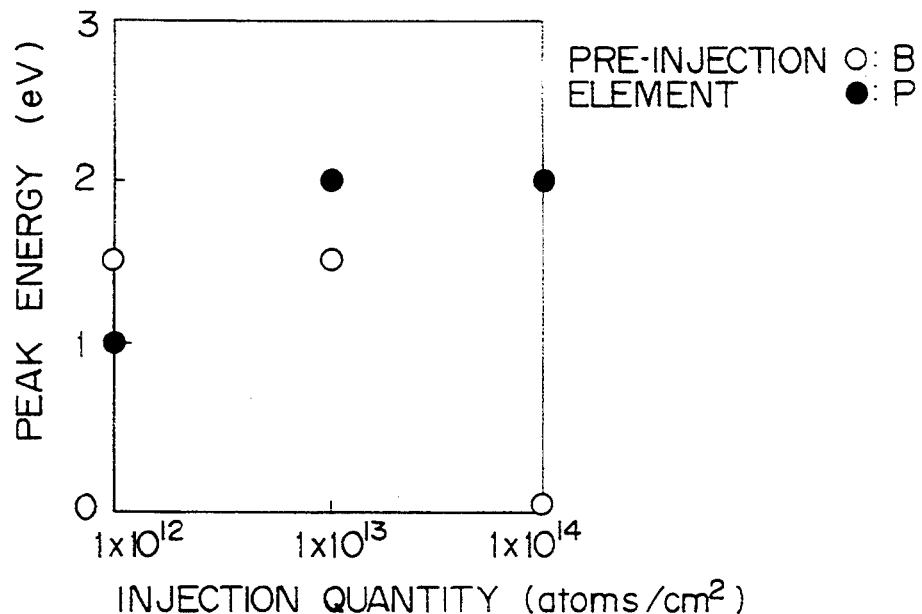
FIGS. 20(a) to (d) are explanatory views each useful for explaining the relationship between a shift quantity of peak energy and an injection quantity of an electrically conductive impurity.
Figure 20B:
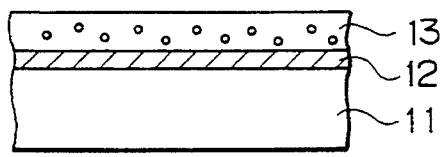
Figure 20C:
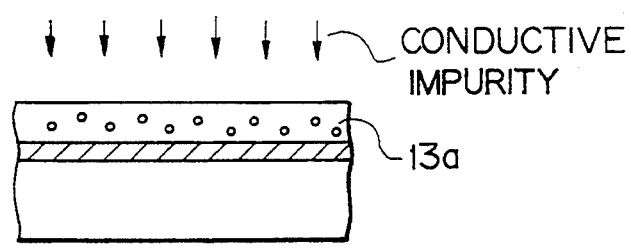
Figure 20D:
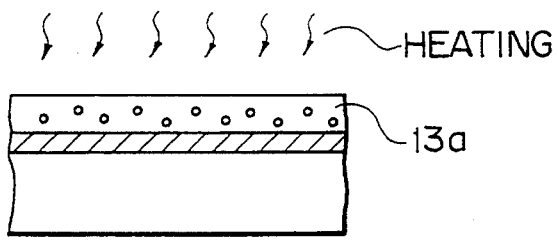

Preparation of Standard Sample According to the Embodiment of the Present Invention FIGS. 20(b) to (d) are sectional views useful for explaining the preparation method of a testpiece used for an electrical charge up test.

FIG. 20(b) shows the state where a 50 nm-thick silicon dioxide film 12 was first formed on an Si substrate 11 by thermal oxidation and then a 400 nm-thick polysilicon film 13 was formed on the silicon dioxide film 12. By the way, the polysilicon film 13 was electrically insulated on this substrate so that charging up could easily take place particularly in or on the polysilicon film 13.

Six of the substrates described above were prepared. As shown in FIG. 20(c), ion implantation was carried out into these six substrates under the following conditions, respectively, and six kinds of testpieces were produced.

(a) electrically conductive impurity (pre-implantated element: boron (B): three kinds of doses, i.e. $1 \times 10^{12}$, $1 \times 10$ and $1 \times 10^{14}$ cm$^{-2}$ (b) electrically conductive impurity (pre-injection element: phosphorus (P): three kinds of doses, i.e. $1 \times 10^{12}$, $1 \times 10^{13}$ and $1 \times 10^{14}$ cm$^{-2}$ Subsequently, each of these substrates was heat-treated at 900° C. for 60 minutes under a nitrogen atmosphere as shown in FIG. 20(d) so as to activate the implanted conductive impurity. In this way, the testpieces were completed.

Figure 21A:
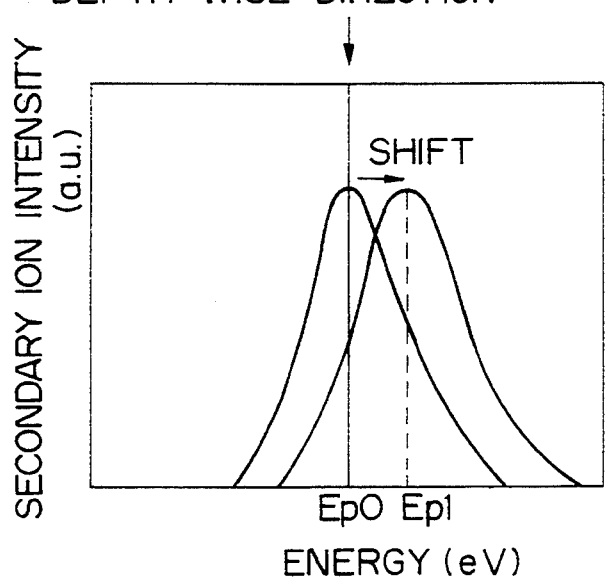
FIGS. 21(a) and (b) are explanatory views each useful for explaining a measurement method of an electrically conductive impurity of a standard sample.
Figure 21B:
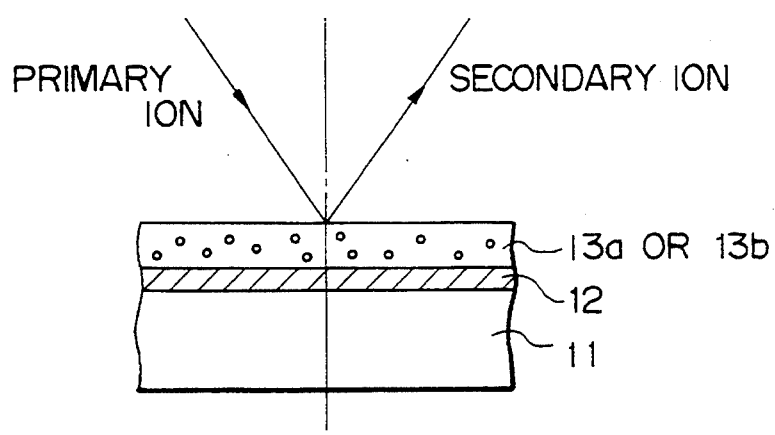
Figure 23:
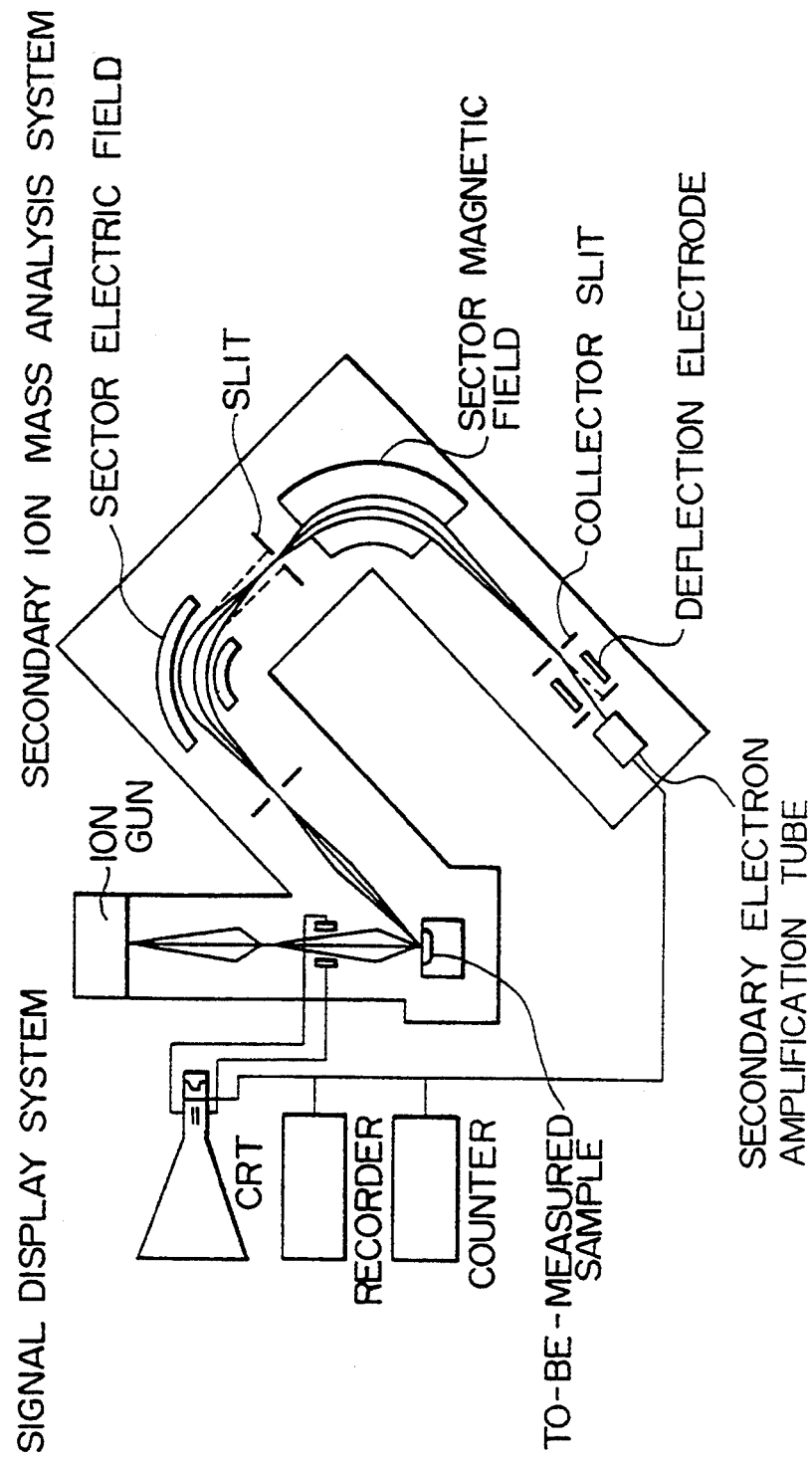
FIG. 23 is an explanatory view useful for explaining a secondary ion mass spectrometer.
Figure 24:
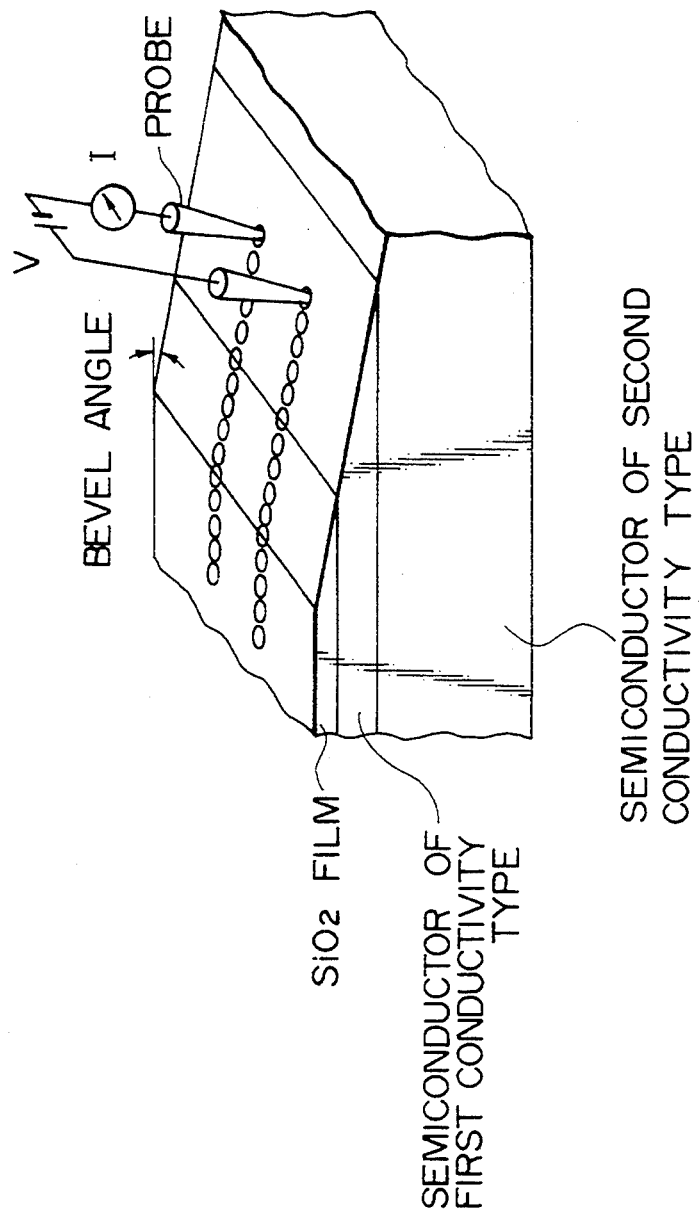
FIG. 24 is a perspective view useful for explaining a spreading resistance analysis method according to the prior art.

Next, one of the testpieces was set into a secondary ion mass spectrometer as shown in FIG. 23. Then, oxygen as the primary ion was irradiated to the surface of the testpiece as shown in FIG. 21(b). At this time, the secondary ions of the conductive impurity having various energy levels jumped out from the surface of the testpiece, and energy of the secondary ions to be detected was changed by regulating an offset voltage to be applied to the sample stage. In this way, the secondary ions having various levels of energy were sequentially measured, and an energy distribution of the intensity of the secondary ions was acquired. At this time, peak energy of each testpiece was measured by setting energy at the peak position of the secondary ion intensity emitted from the sample, which was not electrically charged (hereinafter referred to as the "peak energy"), Ep0, to zero, and using this as the reference. The result is shown in the graph of FIG. 20(a).

According to this result, when the pre-implantation element was boron, a shift of peak energy Ep1 of about 1.5 eV existed at the dose of $1 \times 10^{12}$ cm$^{-2}$ and $1 \times 10^{13}$ cm$^{-2}$. In contrast, peak energy Ep0 became zero at a dose of $1 \times 10^{14}$ cm$^{-2}$.

On the other hand, when the pre-implantation element was phosphorus, peak energy did not become zero at any dose (FIG. 20a). In other words, it was understood that the testpiece was always charged electrically and phosphorus was not suitable as a conductive impurity to be implanted in advance.

Accordingly, it became necessary to dope in advance boron in a dose of at least about $1 \times 10^{14}$ cm$^{-2}$ into the standard sample.

EXAMPLE 7

Preparation of a Standard Sample Used for the Evaluation of Carrier Concentration According to the Present Invention Next, the preparation method of the standard sample according to an embodiment of the invention and a method of converting the intensity of the secondary ions to the concentration of the conductive impurity using the standard sample will be explained.

Figure 19A:
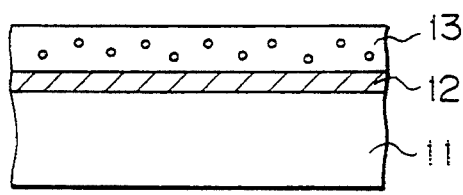
FIGS. 19(a) to (d) are sectional views, each useful for explaining a preparation method of a standard sample.
Figure 19B:
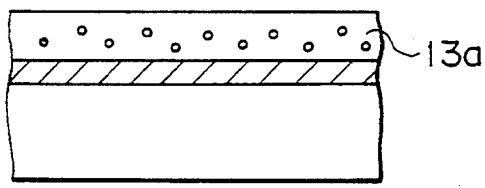
Figure 19C:
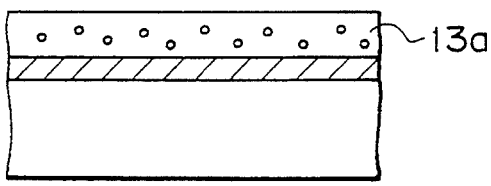

First of all, a substrate having a polysilicon film 13a, into which boron (the pre-implantation element) in an amount of about $2 \times 10^{18}$ cm$^{-3}$ (substantially corresponding to $1 \times 10^{14}$ cm$^{-2}$ when calculated into a dose)

was in advance introduced, was prepared in the same way as in FIGS. 20(b) to (d) (FIGS. 19(a) to (c)).

Figure 19D:
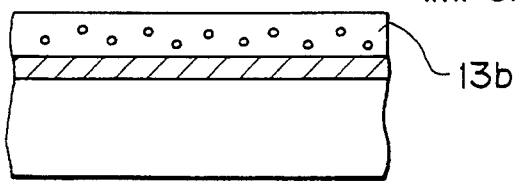

Next, boron ions were implanted into the substrate under the same ion implantation conditions as those for that boron (the same dose and acceleration energy). In this way, the preparation of the standard sample, into which a known quantity of boron was introduced into the polysilicon film 13b, was completed as shown in FIG. 19(d).

Next, the standard sample was set to the secondary ion mass spectrograph shown in FIG. 23. Before the measurement was started, the voltage of the sample stage was in advance regulated to peak energy Ep0 of the secondary ion intensity emitted from a sample not charged electrically.

Subsequently, oxygen as the primary ions was irradiated to the surface of the standard sample. At this time, secondary ions having various levels of energy jumped out from the surface of the standard sample, but only the secondary ions having specific energy Ep0 were detected by the impression or application of the voltage to the sample stage. After the passage of a predetermined time, the intensity of the secondary ions was measured. The intensity of the secondary ions was sequentially measured with the passage of the irradiation time of the primary ions by such a measurement method. In this case, since boron was in advance injected into the standard sample and its resistivity was lowered, charging up did not occur during the measurement. Accordingly, since the shift of the energy distribution of the secondary ion intensity did not occur, the peak value of the secondary ion intensity distribution could be measured at all the measurement points.

Next, the etching quantity corresponding to the irradiation time was plotted on the abscissa and the intensity of the secondary ions, on the ordinate. In this way, the distribution of the intensity Is(x) of the secondary ions in the depth-wise direction could be obtained.

A proportional coefficient A could be obtained in accordance with the following equation on the basis of the graph obtained in the manner described above:

$$\phi = A \cdot \Sigma Is(x) dx \quad (1)$$

where $\phi$: total dose=dose×dose time, A: proportional coefficient.

Using this proportional coefficient A, the concentration N(x) of the carrier and the conductive impurity at a certain depth x could be obtained in accordance with the following equation (2):

$$N(x) = A \cdot Is(x) \quad (2)$$

The concentration N(x) of the carrier and the conductive impurity at a certain depth x can be obtained by using the equation (2). Accordingly, the concentration distribution of the carrier and the conductive impurity can be determined in the depth-wise direction by effecting conversion for all of Is(x) measured with the passage of the irradiation time.

According to the preparation method of the standard sample of the present invention, the resistivity of the poly-silicon film 13a was lowered by introducing, in advance, boron before the known quantity of boron was introduced into the poly-silicon film 13. For this reason, electrical charge up did not occur in the poly-silicon film 13b at the time of the measurement of the intensity of the secondary ions after the known quantity of boron was introduced into the poly-silicon film 13a. In other words, since the shift of the energy distribution of the secondary ion intensity did not occur, the peak value of the secondary ion intensity could be measured at all the measurement points.

Because the concentration of boron, which was introduced in advance, was set to be lower than the concentration of the known quantity of the boron concentration, which was to be measured, the known quantity of the boron concentration to be measured could be measured without being affected by the concentration of boron introduced in advance.

Accordingly, the proportional coefficient A, at a high level of accuracy, could be acquired and, eventually, the concentration distribution of the carrier and the conductive impurity in the depth-wise direction could be acquired with a high level accuracy for the object material to be measured.

Incidentally, boron could be used as the conductive impurity introduced in advance, but a conductive impurity different from the known quantity of the conductive impurity to be measured could also be used.

COMPARATIVE EXAMPLE 1

Figure 22A:
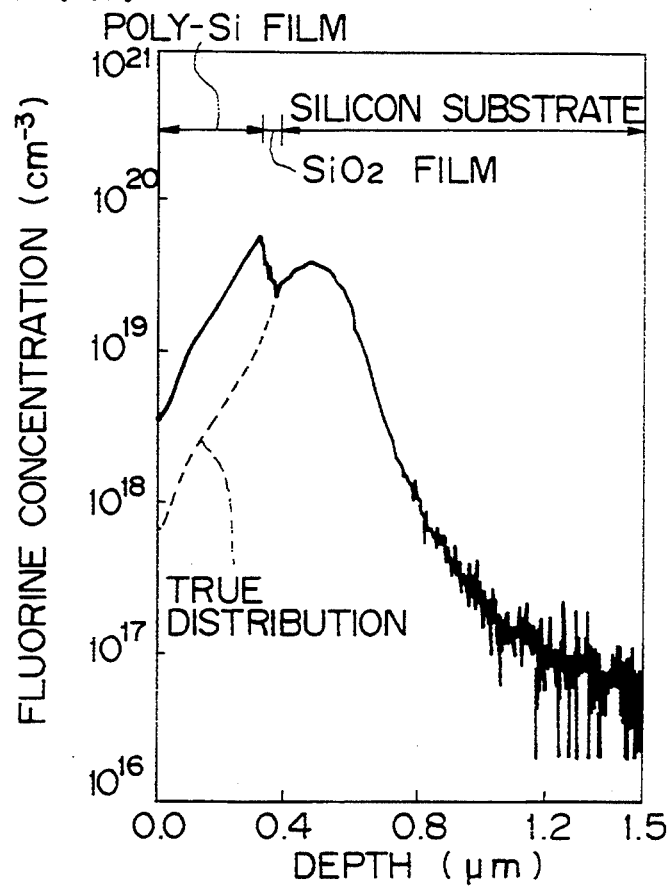
FIGS. 22(a) to (c) are explanatory views each useful for explaining the measurement result of an impurity concentration of the standard sample.
Figure 22B:
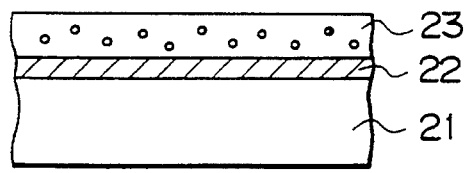
Figure 22C:
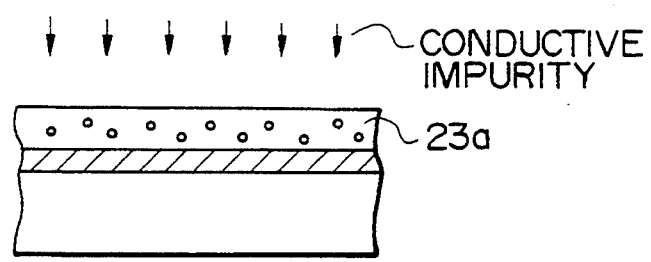

FIGS. 22(b) and (c) are sectional views useful for explaining the preparation method of the standard sample according to a Comparative Example, and fluorine ($^{19}$F) was introduced as an impurity into the standard sample. Unlike the standard sample of the Examples of the present invention, however, the conductive impurity was not introduced in advance into the poly-silicon film and fluorine ($^{19}$F) was introduced under the state where the resistivity was high.

FIG. 22(a) shows the result of measurement by the secondary ion mass spectrometry of the concentration distribution of fluorine ($^{19}$F) in the standard sample.

In FIG. 22(a), the fluorine concentration in the poly-silicon film 23 and the silicon dioxide film 22 indicated a higher concentration than the true concentration distribution. This was presumably because the energy distribution of the secondary ion intensity shifted as shown in FIG. 21(a) and a measurement error occurred.

EXAMPLE 8

Figure 15A:
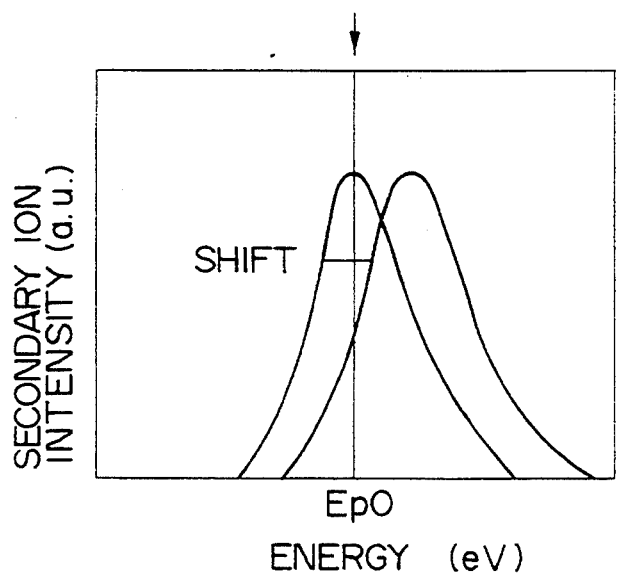
FIGS. 15(a) and (b) are explanatory views each useful for explaining a measurement method of a carrier concentration.
Figure 15B:
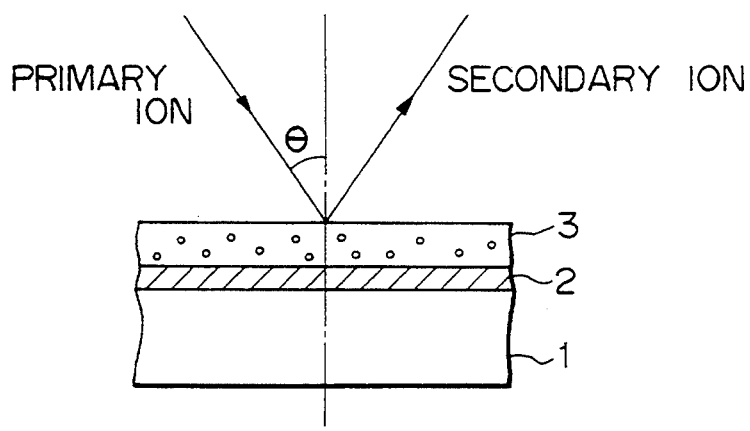

Measurement of Carrier Concentration Distribution in a Semiconductor According to the Invention FIG. 15(b) is a sectional view useful for explaining a test body used for the evaluation of the carrier concentration according to an embodiment of the present invention.

First of all, a 50 nm-thick silicon dioxide film 2 was formed on an Si substrate 1 by thermal oxidation, and then a 400 nm-thick poly-silicon film 3 was formed on the silicon dioxide film 2. Incidentally, the poly-silicon film 3 was electrically insulated from this substrate so that electrical charge up could easily occur particularly in or on the poly-silicon film 3.

Next, boron (B) was introduced as an electrically conductive impurity in a dose of $1 \times 10^{15}$ cm$^{-2}$ into the poly-silicon film 3 by ion implantation.

Each sample was heat-treated at 900° C. for 60 minutes under a nitrogen atmosphere so as to activate the injected conductive impurity. In this way, the test body was completed.

Next, the test body was placed in the secondary ion mass spectrograph shown in FIG. 23. Before the measurement was started, the voltage of the sample stage was in advance regulated to peak energy Ep0 of the secondary ion intensity emitted from the uncharged sample.

Subsequently, oxygen, as the primary ion, was irradiated to the surface of the poly-silicon film 3 under the condition where charge occurred on the surface of the poly-silicon film 3 at all the measurement points of time, that is, at an angle of incidence of $\Theta = 22°$ to the normal of the surface of the poly-silicon film 3. The secondary ions of boron having various energy levels jumped out from the surface of the poly-silicon film 3, but only the secondary ions having specific energy Ep0 were detected by the impression or application of the voltage on the sample stage. After the passage of a predetermined time (t), the intensity I(t) of the secondary ions was measured.

Since the primary ions were irradiated under the condition where electrical charge up took place, that is, at an angle of incidence of $\Theta = 22°$, the poly-silicon film 3 was electrically charged while depending on the carrier concentration. The energy distribution of the secondary ion intensity I(t) shifted to the high energy side or to the low energy side depending on the charge up quantity as shown in FIG. 15(a). At this time, the shape of the energy distribution was hardly affected by the shift of the energy distribution and moreover, only the secondary ions having specific energy Ep0 were detected. Accordingly, the intensity I(t) of the secondary ions corresponding to the carrier concentration could be measured.

The intensity I(t) of the secondary ion was sequentially measured during the irradiation time by such a measurement method. The results were shown in the graph of FIG. 16(a). The axis of abscissa represents the irradiation time and the ordinate represents the secondary ion intensity.

After a series of secondary ion intensity values I(t) were measured, the etching quantity corresponding to the irradiation time was derived, and the intensity I(x) of the secondary ions corresponding to the depth was acquired.

Next, the intensity I(x) of the secondary ions measured was converted to the carrier concentration C(x) in accordance with the equation (2) using the proportional coefficient A determined in advance from the standard sample described above. In this way, the carrier concentration distribution in the depth-wise direction, which corresponds to FIG. 16(a), could be obtained.

Figure 17:
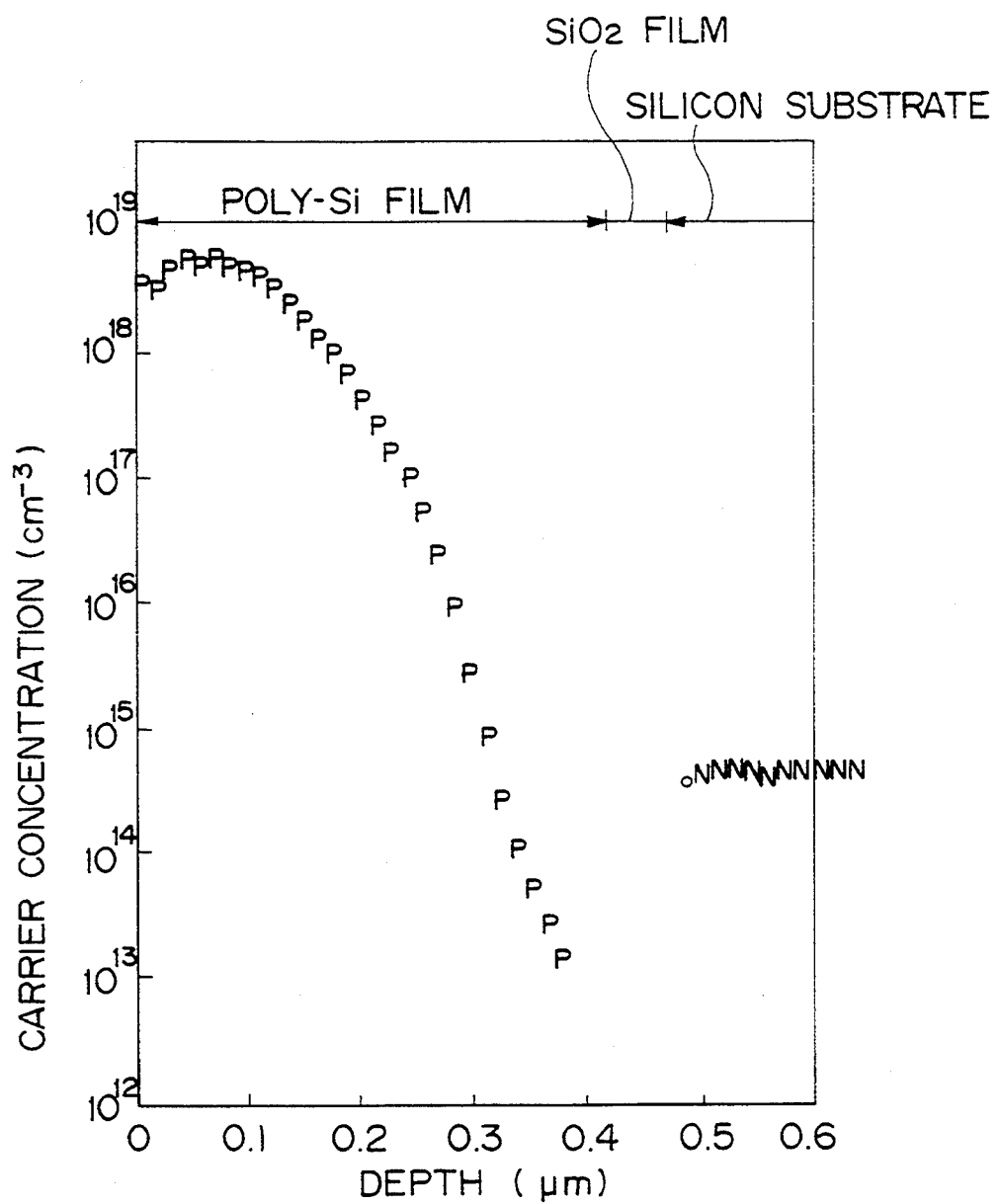
FIG. 17 is a graph showing a measurement result of a carrier concentration distribution by a spreading resistance analysis method.

For reference, FIG. 17 shows the carrier concentration distribution of the same body which was obtained by the spreading resistance analysis method. The present invention could obtain more precise concentration distribution values.

As described above, the measurement method of the carrier concentration distribution in the embodiment of the present invention utilized the properties that the poly-silicon film 3 was electrically charged by the irradiation of the primary ions at a specific angle of incidence and that the carrier concentration and the charge up quantity of the poly-silicon film 3 had a mutual relationship, and provided a correlation between the carrier concentration and the shift quantity of the energy distribution of the secondary ion intensity. Since the shape of the energy distribution of the secondary ion intensity was hardly affected by the shift of the energy distribution, the intensity of the secondary ions corresponding to the carrier concentration could be measured by measuring the intensity of the secondary ions having a specific energy level.

Accordingly, the carrier concentration distribution in the poly-silicon film 3 in the depth-wise direction could be obtained by converting the intensity of the secondary ions measured during the irradiation time of the primary ions to the carrier concentration.

Since the etching quantity due to the irradiation of the primary ions was used to obtain the position in the depth-wise direction, accuracy could be made higher than the spreading resistance analysis method using the polishing method according to the prior art.

In the embodiment described above, the primary ions were irradiated to the surface of the sample under the condition where electrical charge up occurred on the surface of the poly-silicon film 3, that is, at an angle of incidence of $\theta = 22°$ to the normal of the surface of the poly-silicon film 3. However, the angle of incidence $\theta$ could be set to 30° or below as the condition where charge up occurred on the surface of the sample.

Figure 18:
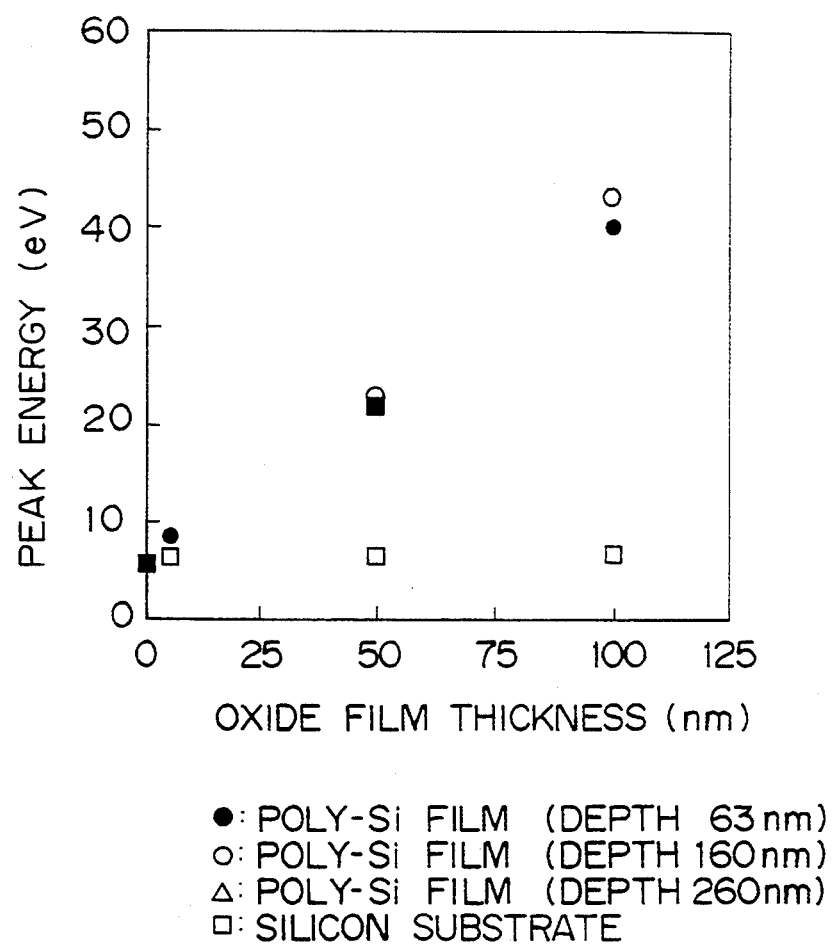
FIG. 18 is a diagram showing the relationship between a shift quantity of peak energy and a thickness of an oxide film of a base.

The thickness of the silicon dioxide film 2 as the base of the poly-silicon film 2 was 50 nm in the embodiment described above, but the thickness could also be set to a suitable film thickness as shown in the drawings. FIG. 18 shows the result of the peak shift energy of the secondary ion mass spectrograph of the poly-silicon film 3 on the silicon dioxide film 2 before the ion injection of the conductive impurity, and illustrates dependence of peak energy on the film thickness of the silicon dioxide film 2. Accordingly, the sensitivity could be regulated through the film thickness of the silicon dioxide film 2.

EXAMPLE 9

Figure 16A:
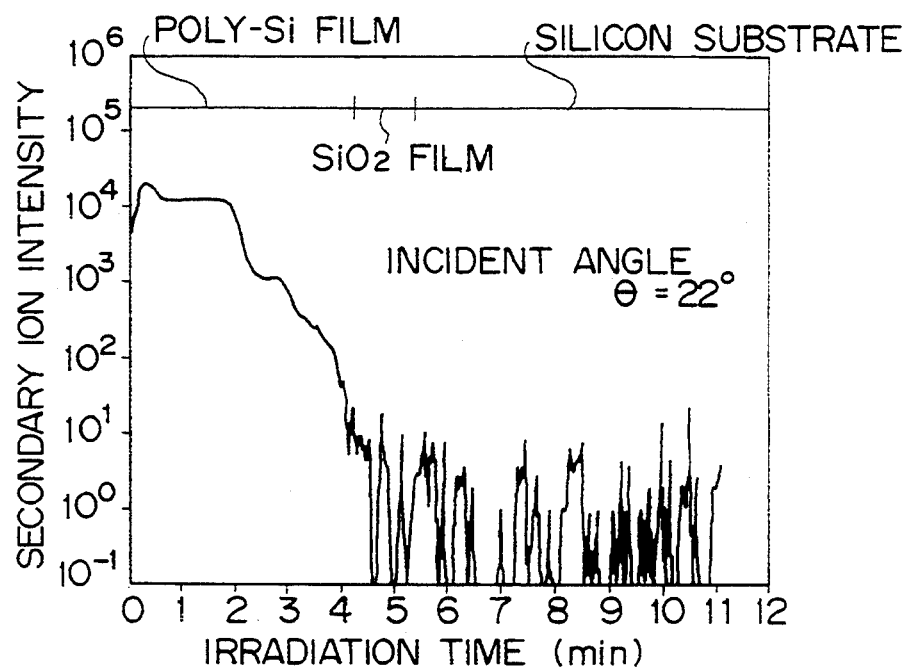
FIGS. 16(a) and (b) are graphs each showing a measurement result of a concentration distribution of a carrier and boron.
Figure 16B:
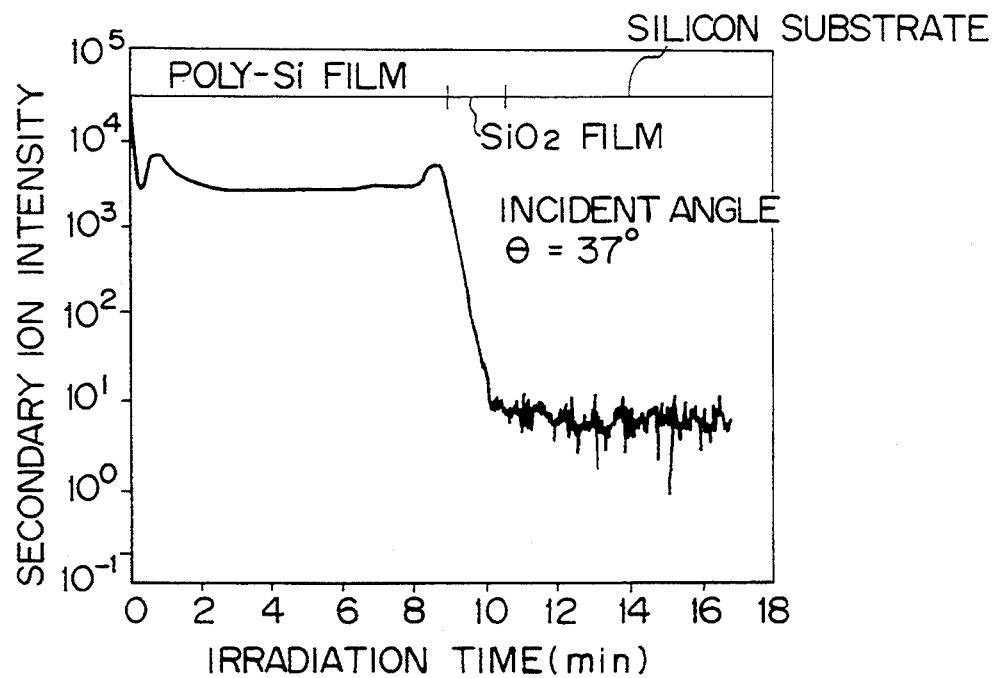

Evaluation of Activation Ratio of Conductive Impurity in Semiconductor According to an Embodiment of the Present Invention FIG. 16(b) shows the result of the measurement of the intensity of the secondary ions measured under the condition where the electrical charge up did not occur on the surface of the poly-silicon film 3, that is, at an angle of incidence $\theta = 37°$, for example, for the sample produced under the same condition as that of the sample shown in FIG. 16(a). However, the axis of abscissa represents the irradiation time of the primary ions. The reason why this irradiation time does not coincide with the irradiation time on the abscissa of FIG. 16(a) is because the etching rate differs with the angle of incidence.

By the way, since the primary ions were irradiated under the condition where electrical charge up did not occur in the poly-silicon film 3, the shift of the energy distribution of the intensity of the secondary ions did not occur. Accordingly, since the peak value of the intensity of the secondary ions could always be measured, the intensity of the secondary ions corresponded to the boron quantity in the poly-silicon film 3.

It can be understood from FIG. 16(b) that boron is distributed in a substantially constant concentration in the poly-silicon film 3. The concentration distribution in the depth-wise direction could be obtained by converting the intensity of the secondary ions to the boron concentration using the standard sample.

The activation ratio could be evaluated by comparing the carrier concentration shown in FIG. 16(a) with the boron concentration shown in FIG. 16(b).

We claim:

1. A measurement method for concentration analysis of a trace element existing in a solid in a planar direction and/or a depth-wise direction, comprising:

irradiating an ion containing an alkali metal element to the surface of said solid as an ion beam;

detecting a three-component atom composite ion comprising said alkali metal ion irradiated, an object element and a base material element from among particles emitted from the surface of said solid due to sputtering by mass separation; and measuring a concentration distribution in the planar direction by displaying an intensity distribution of said three-atom composite ion as a two-dimensional image, or measuring the concentration distribution in the depth-wise direction by displaying the intensity of said three-atom composite ion with a sputtering time.

2. A measurement method according to claim 1, wherein an angle of incidence of said irradiation ion beam is set to from 30° to 90° with respect to the normal of the surface of the solid, in order to improve the sensitivity.

3. A measurement method according to claim 1, wherein an angle of incidence of said irradiation ion beam is set to from 60° to 90° with respect to the normal of the surface of the solid, in order to improve the resolution in the depth-wise direction.

4. A measurement method according to claim 1, wherein an angle of incidence of said irradiation ion beam is set to from 0° to 30° with respect to the normal of the sample, in order to improve resolution in the planar direction.

5. A measurement method according to claim 1, wherein an angle of incidence of said irradiation alkali metal ion beam is set to from 60° to 90° to a solid sample having an oxide film on the surface or between layers thereof, in order to make a high-sensitivity analysis of a trace element contained in said oxide film.

* * * * *